(12) United States Patent
Tonon et al.

(10) Patent No.: US 7,893,019 B2
(45) Date of Patent: Feb. 22, 2011

(54) G-CSF SITE-SPECIFIC MONO-CONJUGATES

(75) Inventors: Giancarlo Tonon, Pula (IT); Gaetano Orsini, Gallarate (IT); Rodolfo Schrepfer, Villa Guardia (IT); Geoffrey Taylor, Pula (IT); Mauro Sergi, Padua (IT)

(73) Assignee: Bio-Ker S.r.l. (IT)

( * ) Notice: Subject to any disclaimer, the term of this patent is extended or adjusted under 35 U.S.C. 154(b) by 0 days.

(21) Appl. No.: 12/310,003

(22) PCT Filed: Jul. 30, 2007

(86) PCT No.: PCT/EP2007/057824

§ 371 (c)(1),
(2), (4) Date: Feb. 6, 2009

(87) PCT Pub. No.: WO2008/017603

PCT Pub. Date: Feb. 14, 2008

(65) Prior Publication Data

US 2010/0029555 A1     Feb. 4, 2010

(30) Foreign Application Priority Data

Aug. 11, 2006 (IT) .......................... MI2006A1624

(51) Int. Cl.
*A61K 38/00* (2006.01)
*C07K 14/535* (2006.01)

(52) U.S. Cl. .......................... 514/1.1; 514/7.6; 530/351

(58) Field of Classification Search .................... None
See application file for complete search history.

(56) References Cited

U.S. PATENT DOCUMENTS

| | | | |
|---|---|---|---|
| 5,985,265 A | 11/1999 | Kinstler et al. | |
| 6,010,871 A | 1/2000 | Takahara et al. | |

FOREIGN PATENT DOCUMENTS

| | | |
|---|---|---|
| EP | 0335423 | 10/1989 |
| EP | 785276 | 7/1997 |
| WO | WO-89/06546 | 7/1989 |
| WO | WO-90/06952 | 6/1990 |
| WO | WO-00/44785 | 8/2000 |
| WO | WO-2005/099769 | 10/2005 |
| WO | WO-2006/019950 | 2/2006 |

OTHER PUBLICATIONS

Satake-Ishikawa et al: "Chemical Modification of Recombinant Human Granulocyte Colony-Stimulating Factor by Polyethylene Glycol Increases Its Biological Activity In Vivo" Cell Struction and Function, Japan Society for Cell Biology (JSCB), Kyoto, JP vol. 17, No. 3 1992, pp. 157-160.
Saifer et al: "Improved Conjugation of Cytokines Using High Molecular Weight Poly(Ethylene Glycol): Peg-GM-CSF as a Prototype" Polymer Preprints, American Cehemcial Society, US, vol. 38, No. 1, 1997, pp. 576-577.
Doherty et al: "Site-specific PEGylation of Engineered Cysteing Analogues of Recombinant Human Ganulocyte-macrophage Colony-stimulating Factor" Bioconjugate Chemistry Sep.-Oct. 2005, vol. 16. No. 5 Sep. 2005 pp. 1291-1298.
Sato et al: "Further Studies on the Site-specific Protein Modification by Microbial Transglutaminase." Bioconjugate Chemistry Sep.-Oct. 2001 vol. 12, No. 5, Sep. 2001, pp. 701-710.
Sato et al: "Site-specific Modification of Interleukin-2 by the Combined use of Genetic Engineering Techniques and Transglutaminase" biochemistry, American Chemical Society. vol. 35, No. 40, Oct. 8, 1996, pp. 13072-13080.

*Primary Examiner*—Robert Landsman
*Assistant Examiner*—Gyan Chandra
(74) *Attorney, Agent, or Firm*—Merchant & Gould, PC

(57) ABSTRACT

Novel site-specific mono-conjugates of Granulocyte Colony Stimulating Factor (G-CSF) are hereby described, with analogues and derivatives thereof, which stimulate proliferation and differentiation of progenitor cells to mature neutrophiles. These conjugates have been obtained using transglutaminase to covalently and site-specifically bind a hydrophilic, non-immunogenic polymer to a single glutamine residue of the human G-CSF native sequence and analogues thereof. These novel site-specific mono-conjugated derivatives are recommended for therapeutic use since they are stable in solution and exhibit significant biological activity in vitro and a longer bloodstream half-life, as compared to the non-conjugated protein, with a consequent prolonged pharmacological activity.

32 Claims, 12 Drawing Sheets

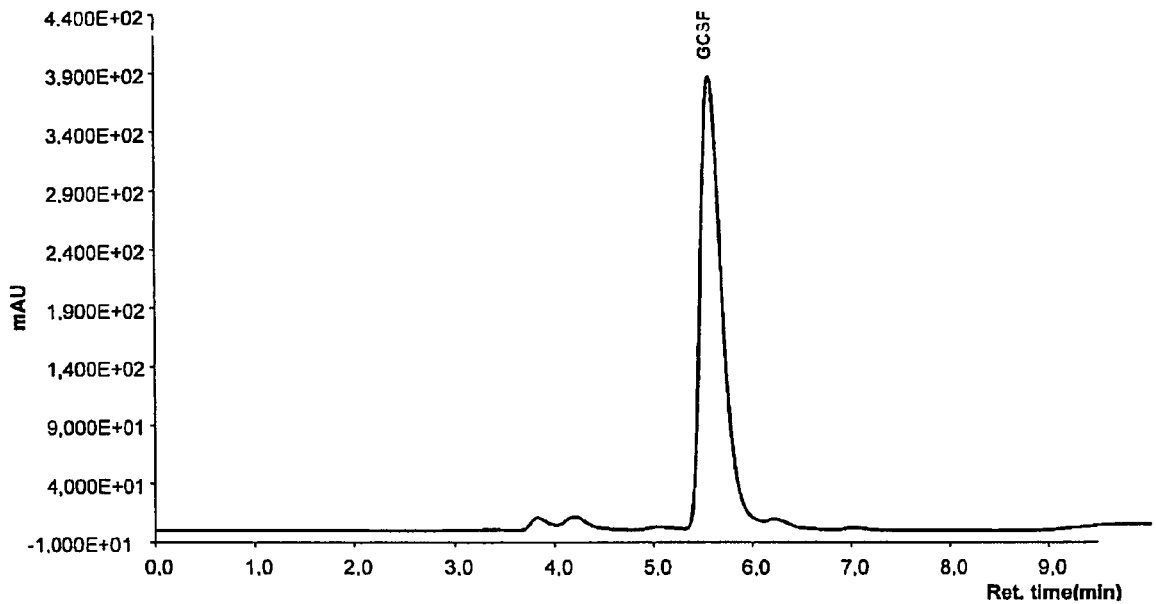
Figure 1 : SE-HPLC chromatogram of G-CSF and PEG 20 kDa reaction mixture in the presence of microbial transglutaminase (MTG), time = 0
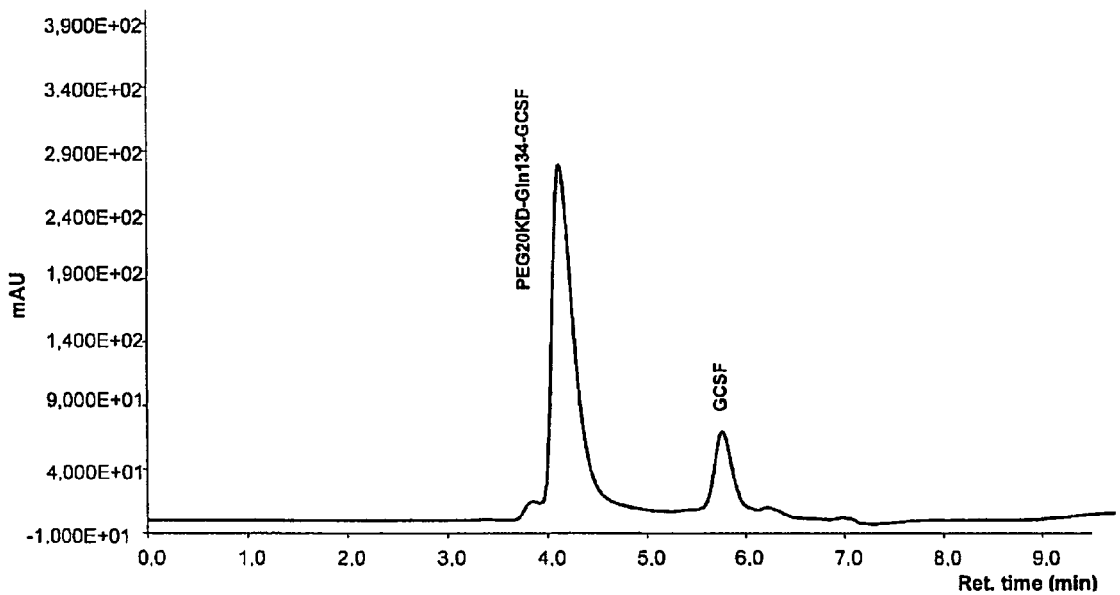
Figure 2 : SE-HPLC chromatogram of G-CSF and PEG 20 kDa reaction mixture in the presence of microbial transglutaminase (MTG), after 16 hours at room temperature

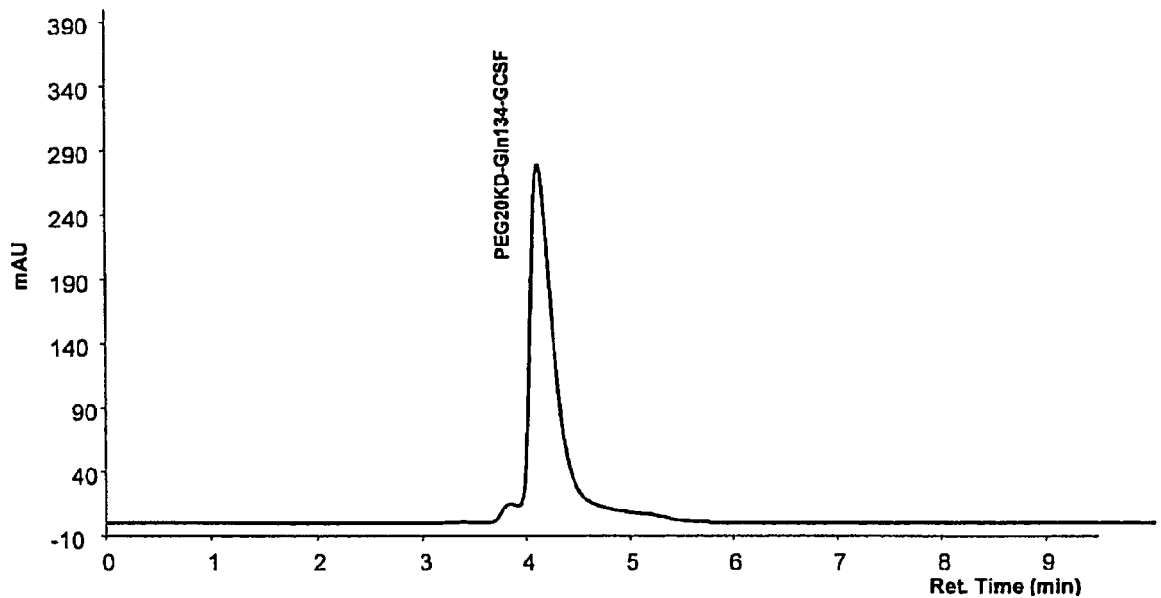
Figure 3 : SE-HPLC chromatogram of G-CSF PEGylated on Gln$^{134}$ after purification
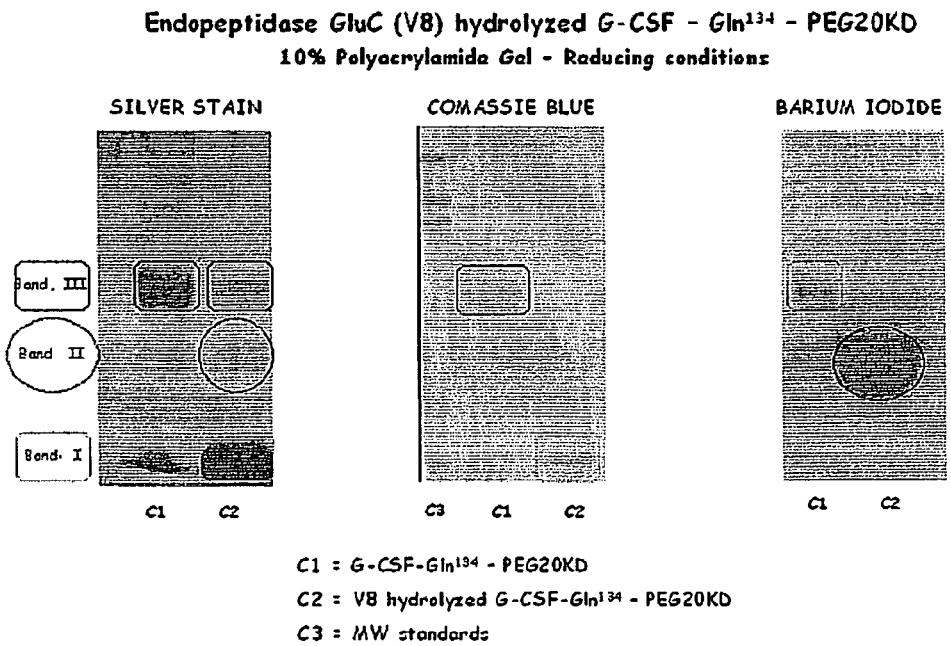
Figure 4 : G-CSF-Gln$^{134}$-PEG20kDa – Hydrolyzed with endopeptidase GluC (V8) Polyacrylamide gel 10 % - reductive condition

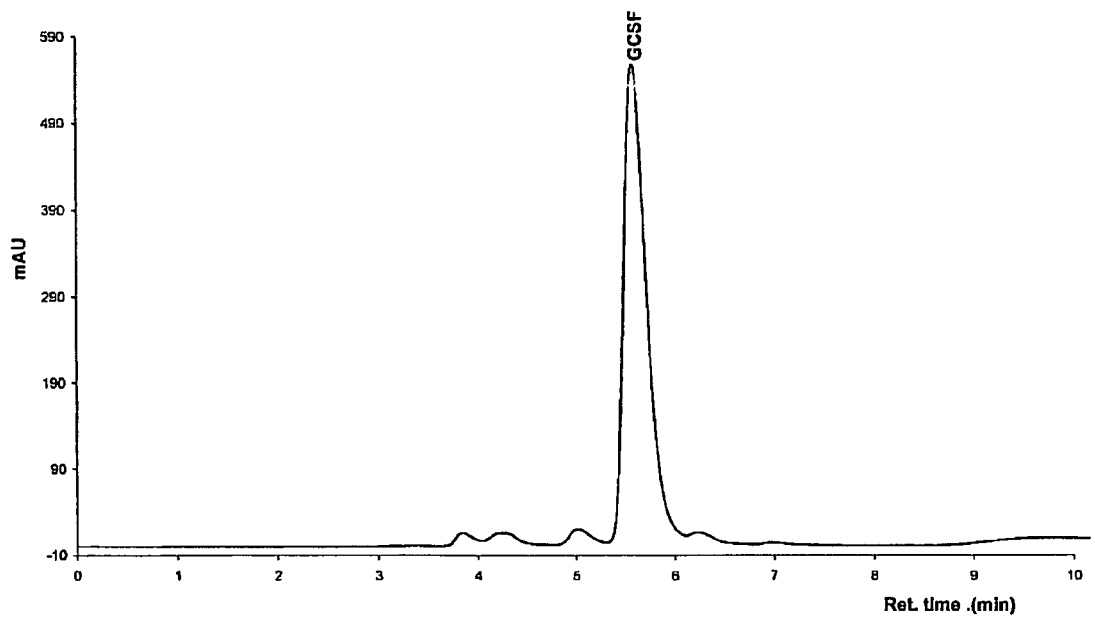
Figure 5 : SE-HPLC chromatogram of Met-G-CSF mutant (Gln 135 -> Asn 135) and PEG 20 kDa reaction mixture in the presence of microbial transglutaminase (MTG), time = 0
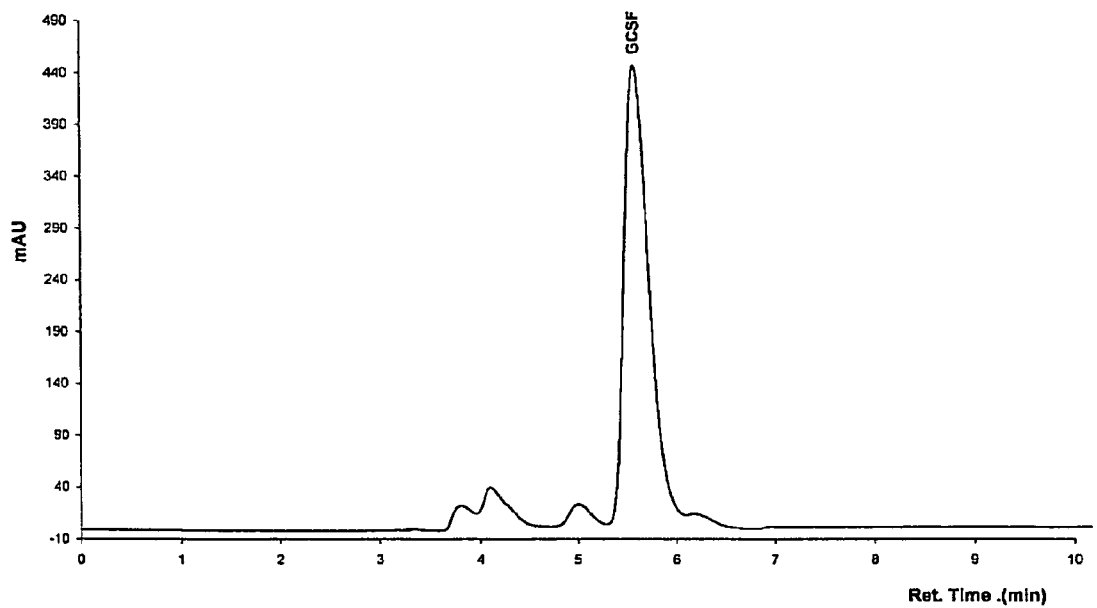
Figure 6 : SE-HPLC chromatogram of Met-G-CSF mutant (Gln 135 -> Asn 135) and PEG 20 kDa reaction mixture in the presence of microbial transglutaminase (MTG), after 16 hours at room temperature

Guinea Pig TG-ase PEGylation
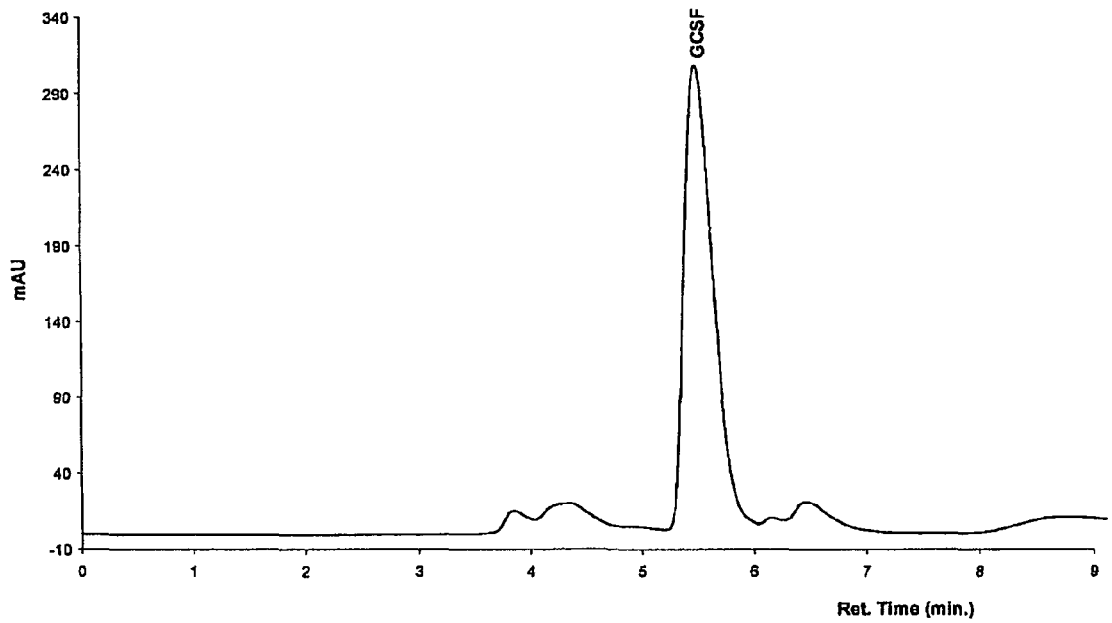
Human Keratinocytes TG-ase PEGylation
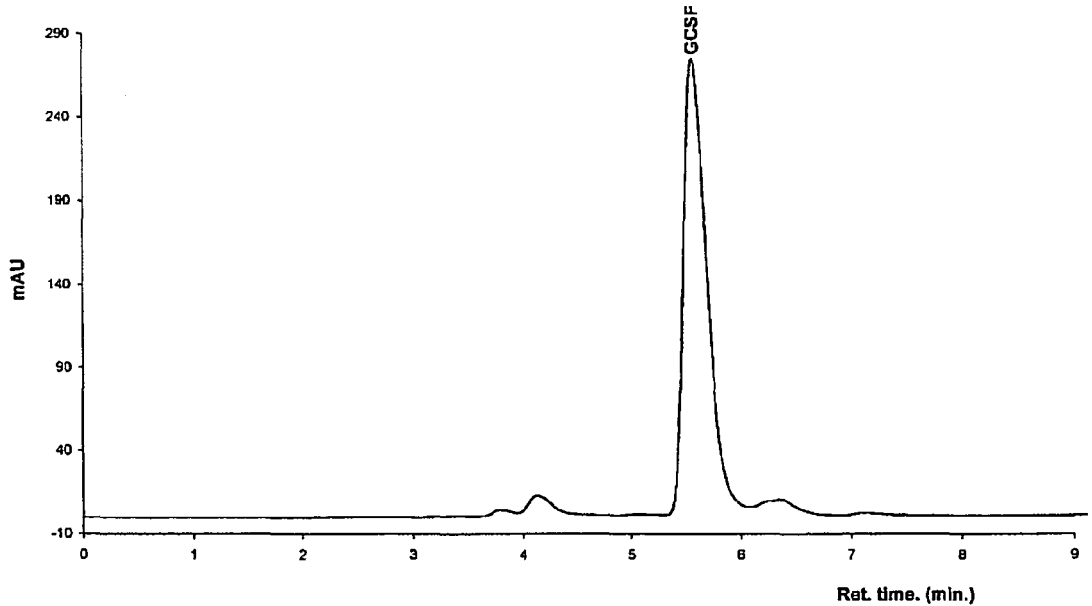
Figure 7 : SE-HPLC chromatogram of G-CSF and PEG 20 kDa reaction mixture in the presence of nonmicrobial transglutaminase (Guinea Pig and human Keratinocytes), time = 0

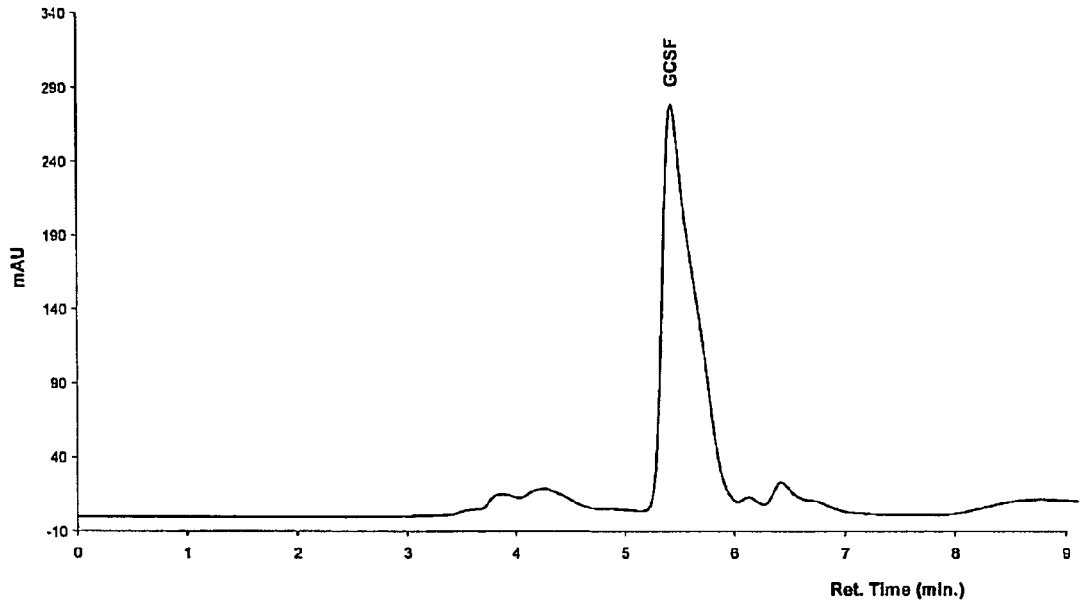
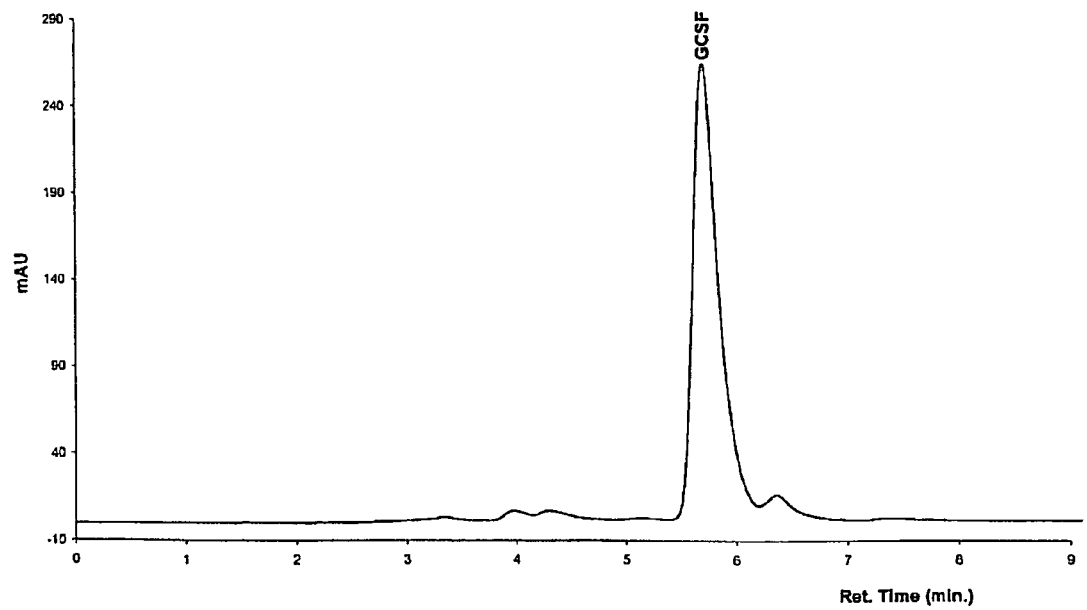
Figure 8 : SE-HPLC chromatogram of G-CSF and PEG 20 kDa reaction mixture in the presence of nonmicrobial transglutaminase (Guinea Pig and human Keratinocytes), after 16 hours at room temperature

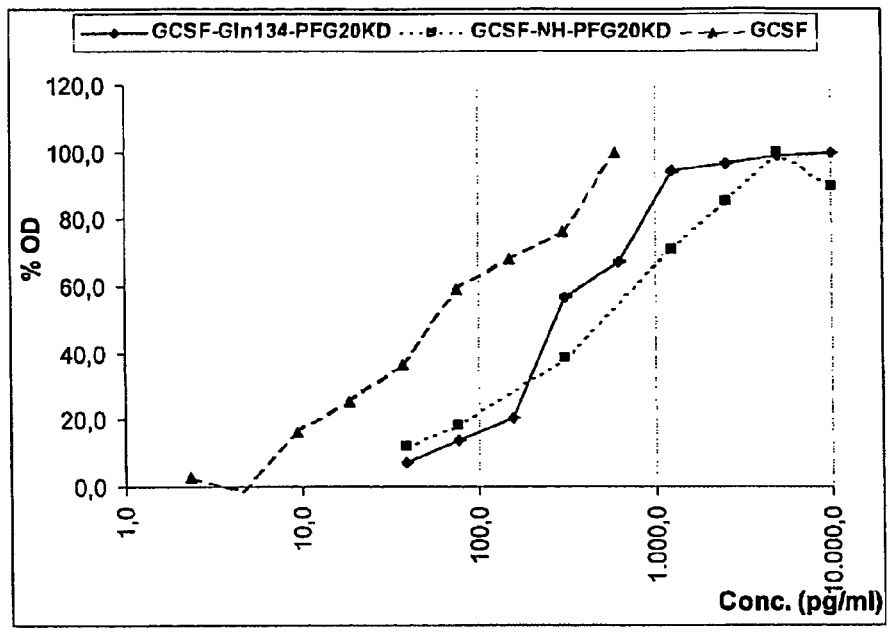
Figure 9 : *In vitro* biological activity. M-NFS60 cells proliferation curves
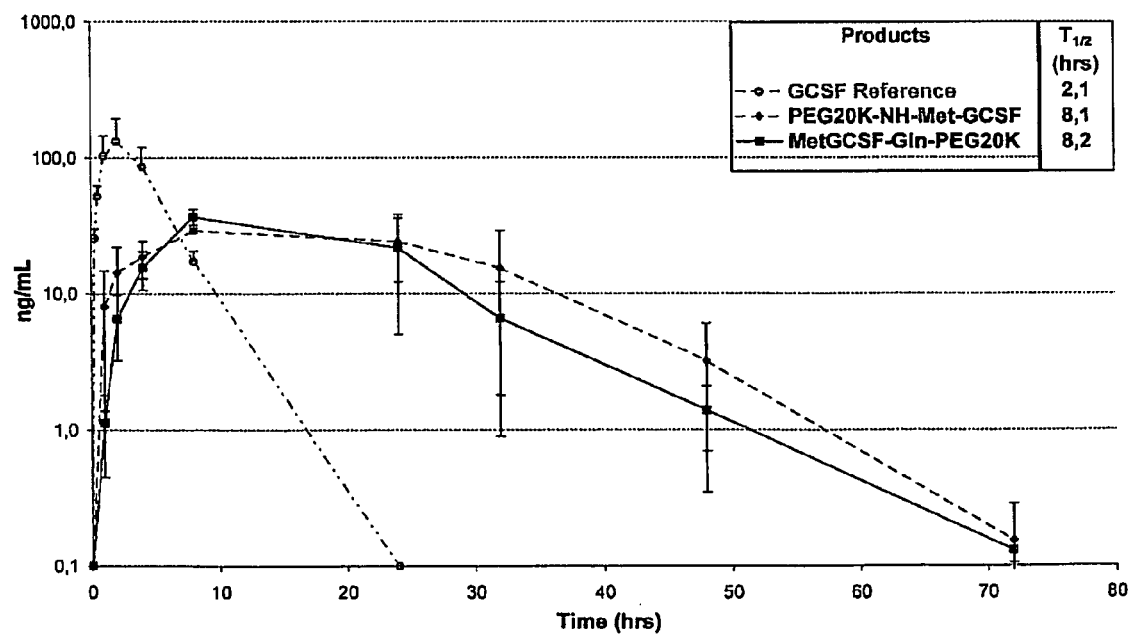
Figure 10 : Pharmacokinetic profiles in rats

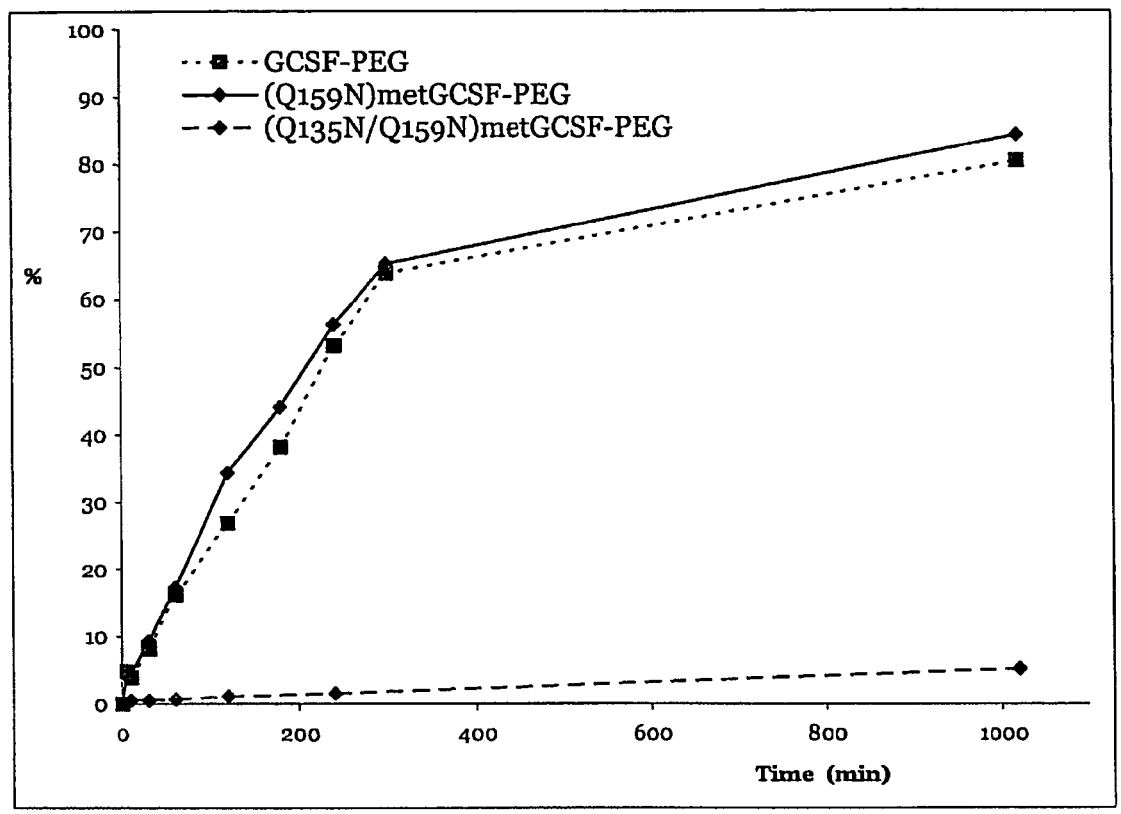
Figure 11 : PEGylation kinetics of Met-G-CSF, Gln159Asn Met-G-CSF and Gln159Asn/Gln135Asn Met-G-CSF

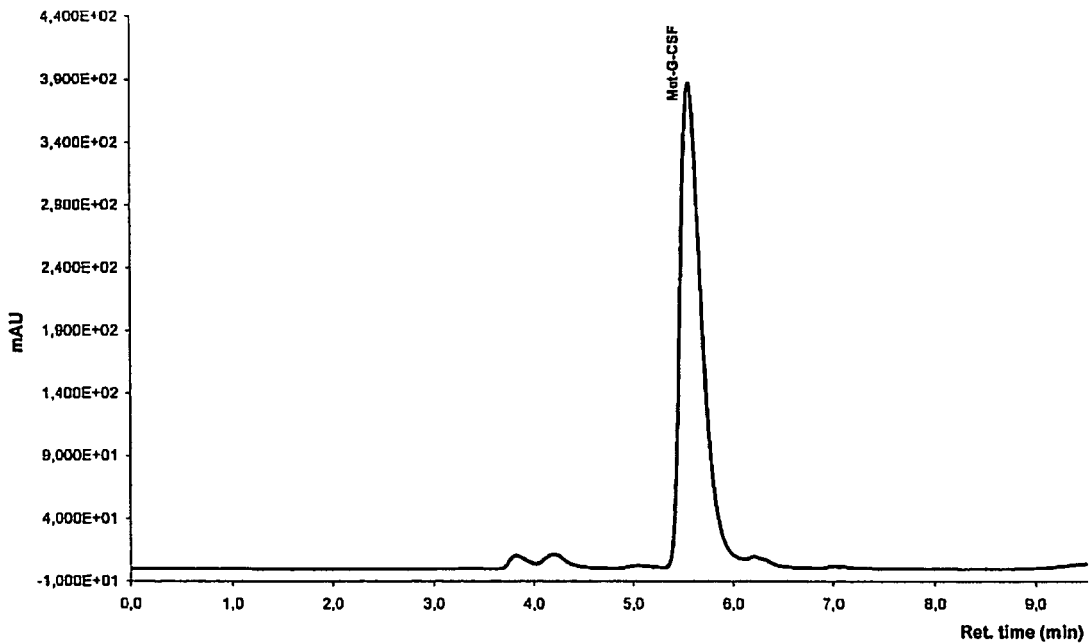
Figure 12: SE-HPLC chromatogram of Met-G-CSF (filgrastim) and PEG 20 kDa reaction mixture in the presence of microbial transglutaminase (MTG), time = 0
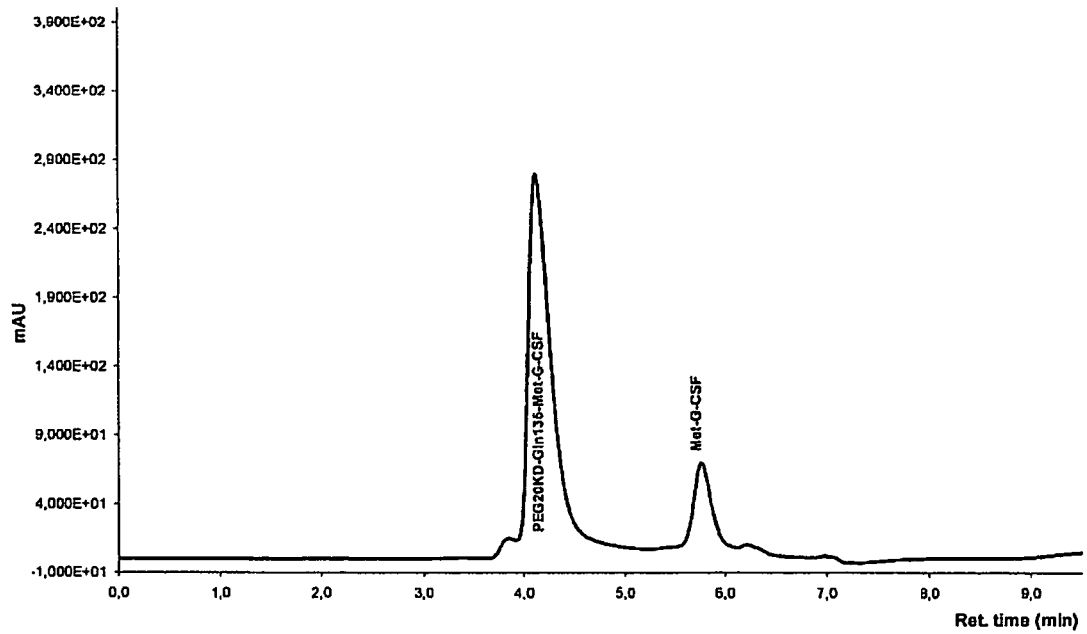
Figure 13: SE-HPLC chromatogram of Met-G-CSF (filgrastim) and PEG 20 kDa reaction mixture in the presence of microbial transglutaminase (MTG), time = 16 hours

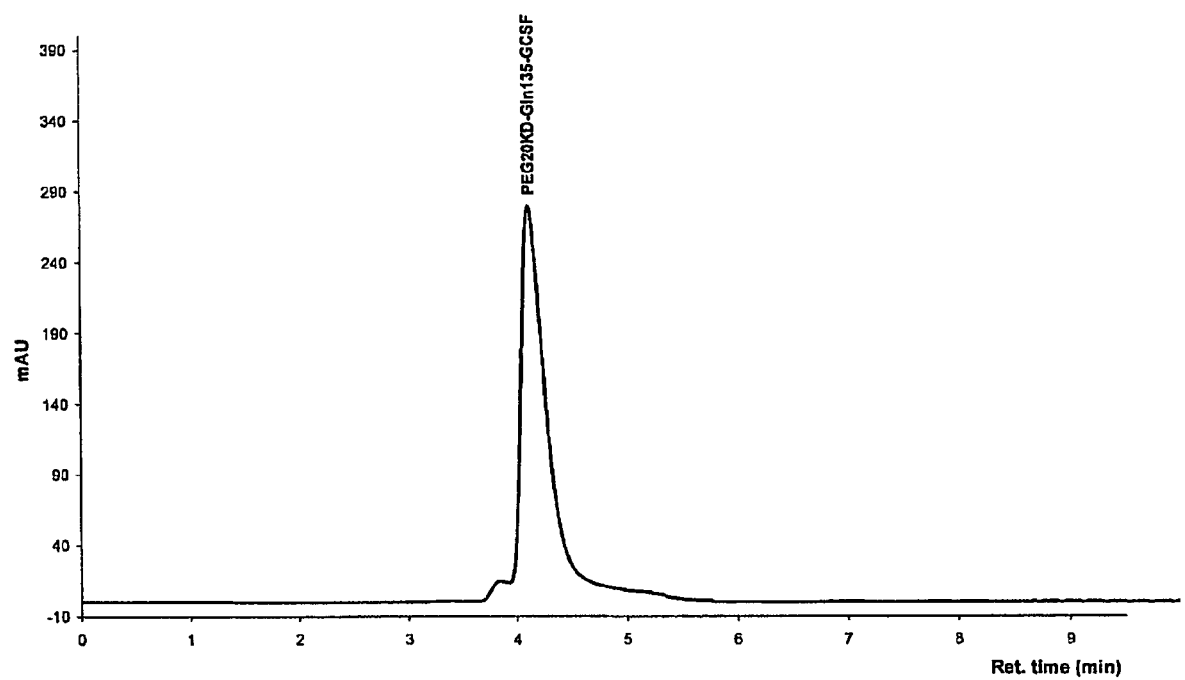
Figure 14: SE-HPLC chromatogram of Met-G-CSF – Gln135 - PEG 20 kDa (filgrastim-Gln135-PEG20KD) after been submitted to purification process

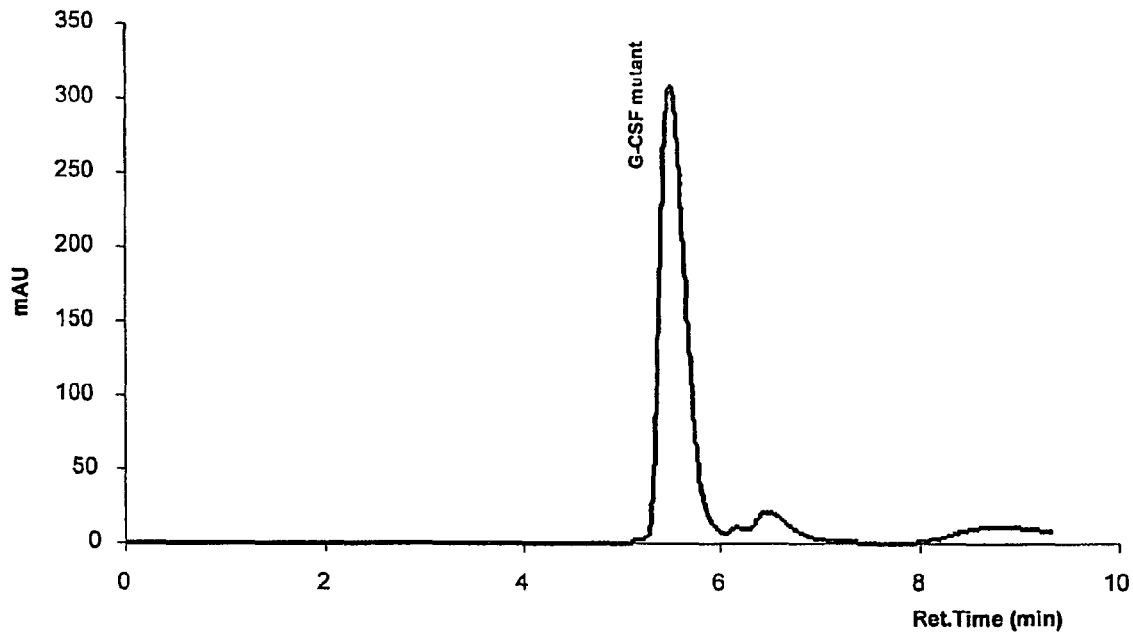
Figure 15: SE-HPLC chromatogram of Gln135Asn Met-G-CSF mutant and PEG 20 kDa reaction mixture in the presence of microbial transglutaminase (MTG), time = 0
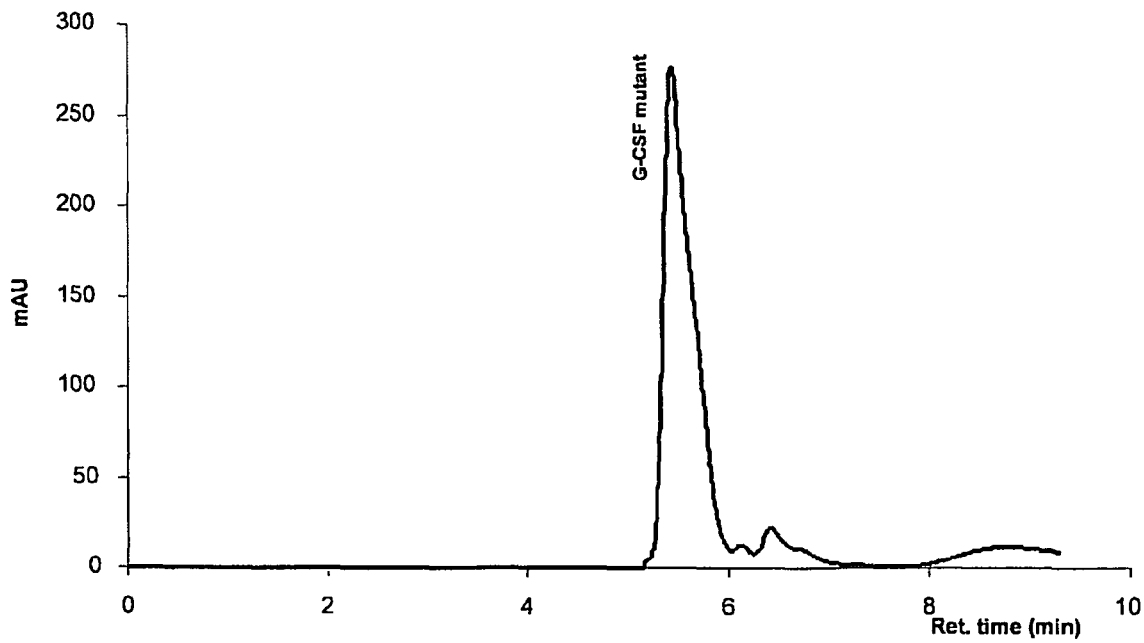
Figure 16: SE-HPLC chromatogram of Gln135Asn Met-G-CSF mutant and PEG 20 kDa reaction mixture in the presence of microbial transglutaminase (MTG), time = 16 hours

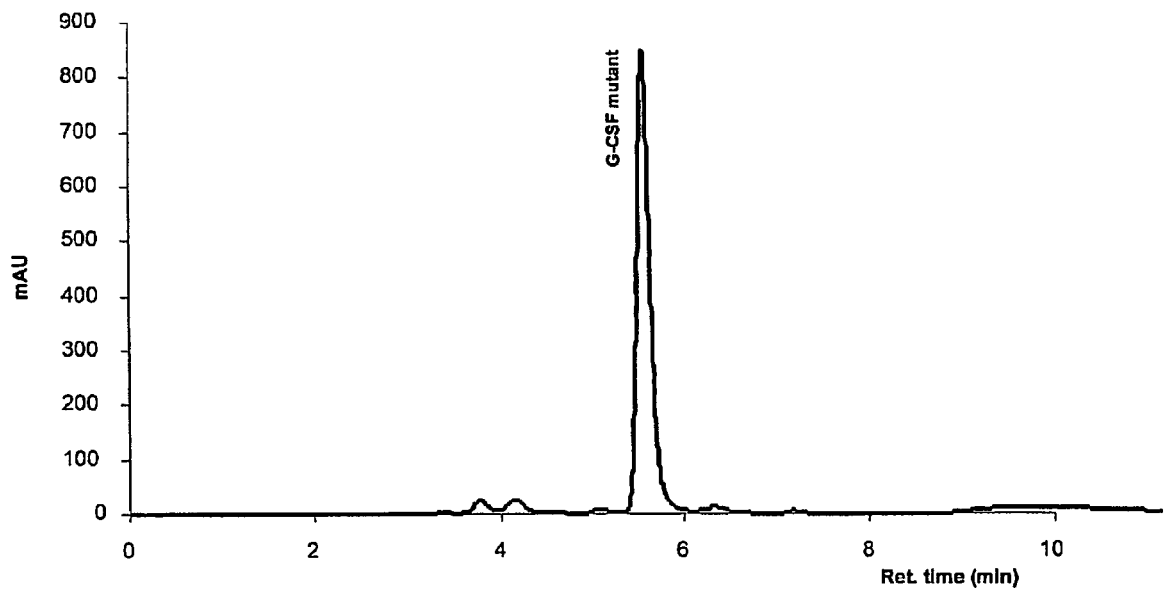
Figure 17: SE-HPLC chromatogram of Gln135Asn-Thr134Gln Met-G-CSF mutant and PEG 20 kDa reaction mixture in the presence of microbial transglutaminase (MTG), time = 0
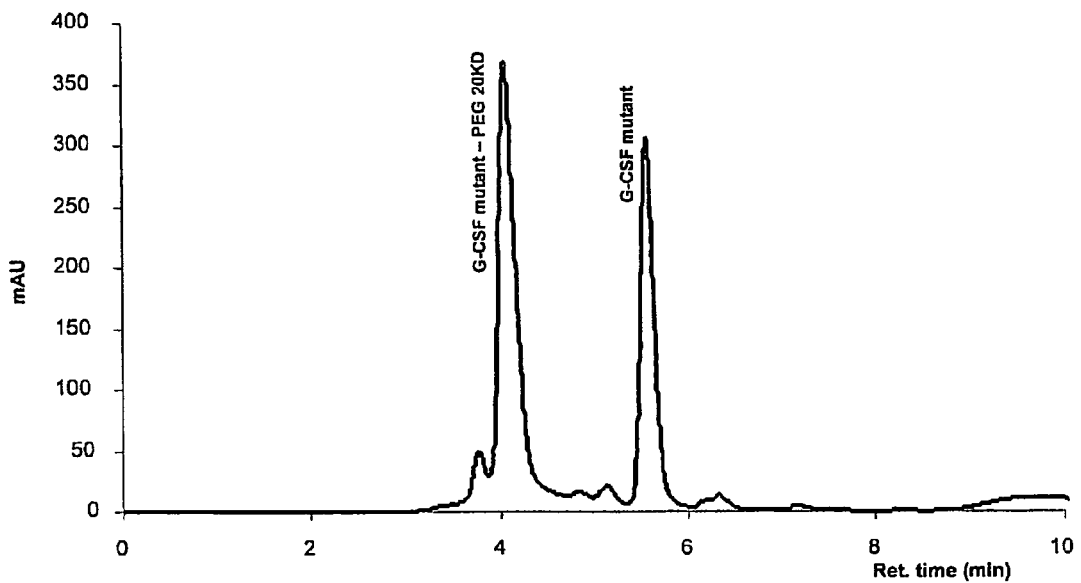
Figure 18: SE-HPLC chromatogram of Gln135Asn-Thr134Gln Met-G-CSF mutant and PEG 20 kDa reaction mixture in the presence of microbial transglutaminase (MTG), time = 16 hours

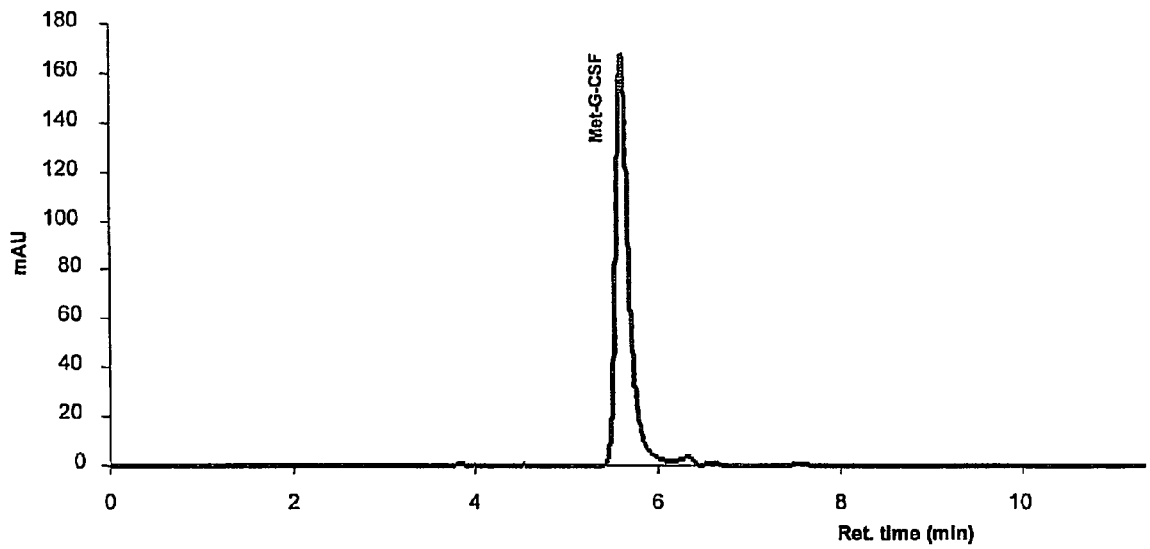
Figure 19: SE-HPLC chromatogram of Met-G-CSF (filgrastim) and PEG 20 kDa reaction mixture in the presence of microbial transglutaminase (250mU/mg of protein), time = 0
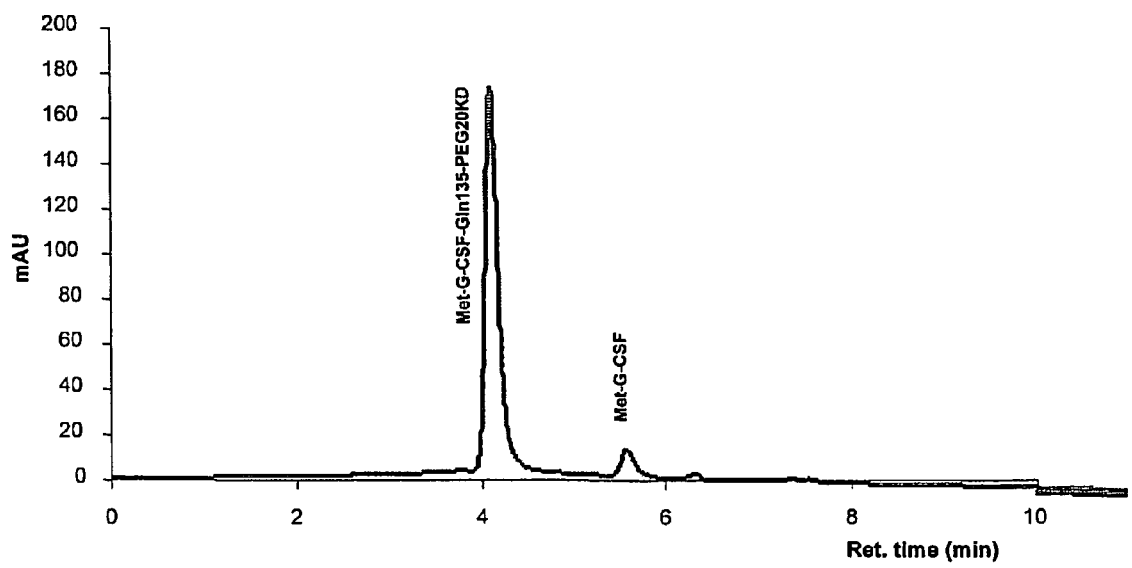
Figure 20: SE-HPLC chromatogram of Met-G-CSF (filgrastim) and PEG 20 kDa reaction mixture in the presence of microbial transglutaminase (250mU/mg of protein), time = 2 hours

G-CSF SITE-SPECIFIC MONO-CONJUGATES

CROSS-REFERENCE TO PRIOR APPLICATIONS

This is a U.S. National Phase Application under 35 U.S.C. §371 of International Patent Application No. PCT/EP2007/057824 filed Jul. 30, 2007, which claims the benefit of Italian Patent Application No. MI2006A001624, filed Aug. 11, 2006, both of which are incorporated by reference herein. The International Application was published in English on Feb. 14, 2008 as WO 2008/017603 A1 under PCT Article 21(2).

Novel site-specific mono-conjugates of Granulocyte Colony Stimulating Factor (G-CSF) are hereby described, with analogues and derivatives thereof, which stimulate proliferation and differentiation of progenitor cells to mature neutrophiles. These conjugates have been obtained using transglutaminase to covalently and site-specifically bind a hydrophilic, non-immunogenic polymer to a single glutamine residue of the native human G-CSF polypeptide sequence and analogues thereof. These novel site-specific mono-conjugated derivatives are recommended for therapeutic use since they are stable in solution and exhibit significant in vitro biological activity and a longer bloodstream half-life, with a consequently prolonged pharmacological activity, compared to the non-conjugated protein.

BACKGROUND OF THE INVENTION

Human Granulocyte Colony Stimulating Factor (h-G-CSF) is a 20 kDa glycoprotein, produced naturally by stromal cells, macrophages, fibroblasts and monocytes. Its production increases upon exposition to endotoxins and during infection. G-CSF acts in the bone marrow, where it binds with high affinity to G-CSF receptors (G-CSFR), expressed on neutrophile precursor cells, by inducing their proliferation and differentiation into mature anti-infective neutrophiles, but without significant hemopoietic effects on other hematic cell lines.

The main native G-CSF isoform is a 174-aminoacid polypeptide having four cysteine residues employed in two disulfide bonds, a free cysteine residue at position 17 and a glycosilation site on the oxygen (O-linked glycosilation) of the threonine residue side chain at position 133. It has been reported that although glycosilation is not necessary to establish an efficient receptorial bond or for G-CSF biological activity (N. A. Nicola, "Hemopoietic Cell Growth Factors and their Receptors", *Ann. Rev. Biochem.*, 58, 45-77, 1989), the presence of the single O-glycosidic chain improves the physical and enzymatic stability of G-CSF (M. Oh-eda et al., "O-linked Sugar Chain of Human Granulocyte Stimulating Factor Protects it against Polymerization and Denaturation Allowing it to Retain its Biological Activity", *J. Biol. Chem.*, 265, 11432-11435, 1990; C. R. D. Carter et al., "Human Serum Inactivates Non-Glycosylated but not Glycosylated Granulocyte Colony Stimulating Factor by a Protease Dependent Mechanism: Significance of Carbohydrates on the Glycosylated Molecule", *Biologicals*, 32, 37-47, 2004). Human G-CSF production by genetic engineering techniques has lead to the development of new therapies to treat several kinds of neutropenia, both primary and secondary. In particular, recombinant G-CSF compounds are prescribed in the hospital setting for the following therapies:

shortening of neutropenia and related infective and febrile phenomena, in high-risk patients being treated with myelotoxic antitumoural drugs or myeloablation followed by bone marrow transplant;

mobilization of peripheral blood progenitor cells to be employed in autologous cell transplant, in patients undergoing myelosuppression or myeloablation, possibly followed by bone marrow transplant;

treatment of patients suffering from congenital or idiopathic neutropenia, showing severe reduction of neutrophile plasmatic concentration, as well as infections and fever;

treatment of neutropenia and bacterial infections, which develop in late-stage HIV infection patients.

The particular interest shown in treating patients affected by different types of neutropenia with G-CSF has stimulated the development of recombinant compounds, produced both in mammalian and bacterial cell systems. In fact, at least three variants of recombinant G-CSF are available in several countries for therapeutic use:

a glycosilated form, called lenograstim, expressed in mammalian cells and engineered as a 174-aminoacid polypeptide chain identical to the native protein polypeptide chain and including an O-linked oligosaccharide moiety on the threonine residue at position 133;

a non-glycosilated form, called filgrastim, expressed in bacterial cells as a 175-aminoacid polypeptide chain identical to the native protein except for an additional methionyl residue at the N-terminal (met-G-CSF);

a non-glycosilated form, called nartograstim, expressed in bacterial cells as a 175-aminoacid polypeptide chain (met-G-CSF) which differs from the native protein polypeptide chain by the additional methionyl residue at the N-terminal, as well as substitution for Thr 2, Leu 4, Gly 5, Pro 6 and Cys 18 residues with, respectively, Ala, Thr, Tyr, Arg and Ser residues.

A limit, well-known in the clinical application of the various recombinant G-CSF derivatives, is the short circulating permanence in the bloodstream after parenteral administration, with a pharmacokinetic half-life ($t_{1/2}$) of 3-4 hours. As a consequence, the dosage of recombinant G-CSF prescribed, for example, to reduce the development of infections in patients having non-myeloid tumours and undergoing myelosuppressive chemotherapy, consists of daily administration of subcutaneous injections of 5 microgram/kg/die G-CSF for the duration of the chemotherapy cycle, amounting to 10-14 injections per cycle.

The G-CSF pharmacokinetic profile, as with the majority of cytokines, is regulated by a non-specific and nonsaturable renal clearance mechanism (and, to a lesser degree, hepatic clearance), in addition to a specific and saturable mechanism of internalization and partial degradation mediated by cells expressing the G-CSF receptor.

Since renal clearance is related to the size of the protein molecule, one way of reducing renal ultrafiltration is to increase the molecular size and/or the hydrodynamic volume.

This is a very common problem in the field of therapeutic proteins and several solutions have been proposed, such as fusion of the therapeutic protein to carrier proteins (for example, immunoglobulin or albumin); incorporation of the active ingredient in slow-release polymer nano- and microspheres; and covalent bond protein conjugation to biocompatible, high molecular weight polymers.

In particular, in the area of covalent protein-polymer conjugation, the so-called PEGylation reaction has been extensively employed, where the chosen protein is covalently bound to one or more linear or branched poly(ethylene glycol) (PEG) chains, having a molecular weight ranging from 1,000-2,000 Da to 20,000-40,000 Da or even higher. In general, PEGylated proteins show lower renal clearance rates, as well as higher stability and reduced immunogenicity. When PEG is suitably bound to a polypeptide, its hydrodynamic volume and physico-chemical properties are modified, while fundamental biological functions, such as in vitro activity or receptor recognition, may remain unchanged, undergo a slight reduction or, in some cases, be completely suppressed. PEG conjugation masks the protein surface and increases its molecular size, thus decreasing renal ultrafiltration, preventing attachment of antibodies or antigen processing cells and reducing proteolytic enzyme degradation. Finally, PEG conjugation confers the physico-chemical properties of PEG and, therefore, peptide and non-peptide drug biodistribution and solubility are similarly modified. As an alternative to PEG for protein conjugation, other linear or branched biocompatible polymers, such as dextran, poly(vinylpyrrolidone), poly (acryloylmorpholine) or polysaccharides may be employed.

For a survey of commonly employed chemical PEGylation techniques and results, reference is made to the following:

S. Zalipsky, Chemistry of Polyethylene Glycol Conjugates with Biologically Active Molecules, *Adv. Drug Deliv. Rev.*, 16, 157-182, 1995;

F. M. Veronese, Peptide and Protein PEGylation: a Review of Problems and Solutions, *Biomaterials*, 22, 405-417, 2001.

G-CSF covalent conjugation to high molecular weight, biocompatible polymers has been described, for example, in several scientific articles and patents, some of which are briefly summarized below.

WO 89/06546 describes a G-CSF genetic variant, chemically conjugated to polymer chains of poly(ethylene glycol) or poly(propylene glycol) which maintains biological activity and shows an enhanced bloodstream half-life.

WO 90/06952 describes a G-CSF modification with PEG chains by chemically binding the amino and carboxyl groups of aminoacid side chains to yield a long half-life PEG-G-CSF conjugate.

WO 00/44785 describes G-CSF derivatives, chemically bound to 1-15 polymer PEG chains where stability, solubility and bloodstream circulation are improved after in vivo administration.

EP0335423 describes PEG-G-CSF chemical conjugates showing different structural, physico-chemical and biological properties.

While the abovementioned conjugates, mainly obtained by nonselective conjugation with G-CSF amino or carboxyl groups, are usually conjugated isoform mixtures, G-CSF chemical conjugates have been developed to yield essentially site-specific, mono-conjugate derivatives, as reported below.

U.S. Pat. No. 5,985,265 describes a method for polymer compound conjugation to the α-amino group of the N-terminal aminoacid residue of a polypeptide chain, which can be obtained both by an amide bond between the polymer and the protein, and, preferably, by an amine bond between the polymer and the protein through a reductive alkylation reaction (O. Kinstler et al., Mono-N-terminal Poly-(Ethylen Glycol)-Protein Conjugates, *Adv. Drug Deliv. Rev.*, 54, 477-485, 2002). Application of this technology has, therefore, allowed development of a met-G-CSF conjugated to a 20 kDa linear PEG on the α-amino group of the N-terminal methionyl by a pH 5 reductive alkylation reaction with a monomethoxy-PEG chain functionalized with propionaldehyde; this product has been marketed with the international non-proprietary name of PEG-filgrastim and the registered brand name of Neulasta® (O. Kinstler et al., Characterization and Stability of N-terminally PEGylated rhG-CSF, *Pharmac. Res.*, 13, 996-1002, 1996).

Another protein residue, which can potentially give rise to site-specific conjugates, is the cysteine thiol group, a highly reactive moiety to PEG molecules functionalized with residues forming a covalent bond with the thiol radical (M. J. Roberts et al., Chemistry for Peptide and Protein PEGylation, *Adv. Drug Deliv. Rev.*, 54, 459-476, 2002). Since most proteins do not have a free cysteine residue (that is, not involved in a disulfide bond), it is possible to site-specifically conjugate polymer and protein by inserting into the polypeptide chain, through site-specific mutagenesis, a cysteine residue which will then permit reaction with the polymer functionalized with the cysteine thiol reactive group, as described for a series of G-CSF mutants (M. S. Rosendahl et al., Site-specific Protein PEGylation. Application to Cysteine Analogs of Recombinant Human Granulocyte Colony-Stimulating Factor, *BioProcess Internat.*, 3 (4), 52-60, 2005).

According to a partially alternative approach, WO 2005/099769A2 describes r-h-G-CSF conjugation on the native cysteine thiol group not involved in disulfide bonds ($Cys^{17}$), after partial protein denaturation, so that the free —SH moiety, otherwise masked in a hydrophobic pocket, is exposed to the solvent.

As well as the various abovementioned chemical conjugation techniques, enzymatic procedures have been described, to bind polymer and protein. These are based on the employment of transglutaminase enzymes, both prokaryotic and eukaryotic, to catalyze the transfer of a polymer, functionalized with a primary amino group, to the acyl groups of glutamine residues, naturally present in the polypeptide chain of interest or inserted via site-specific mutagenesis reactions (H. Sato, Enzymatic Procedure for Site-Specific PEGylation of Proteins, *Adv. Drug Deliv. Rev.*, 54, 487-504, 2002).

Therefore, for instance, both EP785276 and U.S. Pat. No. 6,010,871 describe the use of a microbial transglutaminase (MTG) to insert polymer chains in peptides and proteins with at least one glutamine residue in their aminoacid sequence. In these patents, although examples are given of mono-substitution on some model proteins, it is not clear if the substitutions are also site-specific, meaning whether they yield a single molecular form or a positional isomer mixture where, though mono-substituted, the polymer chains are bound to different glutamines.

BRIEF DESCRIPTION OF THE DRAWINGS

FIG. 1: SE-HPLC chromatogram of G-CSF and PEG20 kDa reaction mixture in the presence of microbial transglutaminase (MTG), time=0.

FIG. 2: SE-HPLC chromatogram of G-CSF and PEG20 kDa reaction mixture in the presence of microbial transglutaminase (MTG), after 16 hours at room temperature.

FIG. 3: SE-HPLC chromatogram of G-CSF PEGylated on $Gln^{134}$ after purification.

FIG. 4: Gel electrophoresis of V8 hydrolyzed G-CSF PEGylated on $Gln^{134}$ with PEG20 kDa.

FIG. 5: SE-HPLC chromatogram of met-G-CSF mutant (Gln 135->Asn 135) and PEG20 kDa reaction mixture in the presence of microbial transglutaminase (MTG), time=0.

FIG. 6: SE-HPLC chromatogram of met-G-CSF mutant (Gln 135->Asn 135) and PEG20 kDa reaction mixture in the presence of microbial transglutaminase (MTG), after 16 hours at room temperature.

FIG. 7: SE-HPLC chromatogram of G-CSF and PEG20 kDa reaction mixture in the presence of nonmicrobial transglutaminase (Guinea Pig and human Keratinocytes), time=0.

FIG. 8: SE-HPLC chromatogram of G-CSF and PEG20 kDa reaction mixture in the presence of nonmicrobial transglutaminase (Guinea Pig and human Keratinocytes), after 16 hours at room temperature.

FIG. 9: In vitro biological activity: M-NFS60 cells proliferation curves.

FIG. 10: Pharmacokinetic profiles in rats.

FIG. 11: PEGylated kinetics of met-G-CSF, Gln159Asn Met-G-CSF and Gln159Asn/Gln135Asn met-G-CSF.

FIG. 12: SE-HPLC chromatogram of met-G-CSF (filgrastim) and PEG20 kDa reaction mixture in the presence of microbial transglutaminase (MTG), time=0.

FIG. 13: SE-HPLC chromatogram of met-G-CSF (filgrastim) and PEG20 kDa reaction mixture in the presence of microbial transglutaminase (MTG), time=16 hours.

FIG. 14: SE-HPLC chromatogram of met-G-CSF-Gln135-PEG20 kDa (filgrastim-Gln135-PEG20 kDa) after purification.

FIG. 15: SE-HPLC chromatogram of Gln135Asn met-G-CSF mutant and PEG20 kDa reaction mixture in the presence of microbial transglutaminase (MTG), time=0.

FIG. 16: SE-HPLC chromatogram of Gln135Asn met-G-CSF mutant and PEG20 kDa reaction mixture in the presence of microbial transglutaminase (MTG), time=16 hours.

FIG. 17: SE-HPLC chromatogram of Gln135Asn-Thr134Gln met-G-CSF mutant and PEG20 kDa reaction mixture in the presence of microbial transglutaminase (MTG), time=0.

FIG. 18: SE-HPLC chromatogram of Gln135Asn-Thr134Gln met-G-CSF mutant and PEG20 kDa reaction mixture in the presence of microbial transglutaminase (MTG), time=16 hours.

FIG. 19: SE-HPLC chromatogram of met-G-CSF (filgrastim) and PEG20 kDa reaction mixture in the presence of microbial transglutaminase (250 mU/mg of protein), time=0.

FIG. 20: SE-HPLC chromatogram of met-G-CSF (filgrastim) and PEG20 kDa reaction mixture in the presence of microbial transglutaminase (250 mU/mg of protein), time=2 hours.

DESCRIPTION OF THE INVENTION

The subject of the present invention concerns novel human G-CSF site-specific mono-conjugated derivatives and analogues thereof for therapeutic use, designed to overcome common drawbacks connected with pharmaceutically active proteins, such as high clearance rates and, consequently, reduced blood half-life, susceptibility to proteolytic degradation and potential immunogenic responses.

The G-CSF site-specific mono-conjugated derivatives, subject of the present invention, have been designed to minimize structural and conformational modifications to the protein so as to obtain a conjugated derivative exhibiting a homogeneous physico-chemical profile and optimal pharmacokinetic and pharmacodynamic behaviour. The novel site-specific mono-conjugate derivatives, possessing the abovementioned properties, can be employed as long-lasting equivalents of the normally utilized therapeutic compounds, but with less frequent administration (for example, weekly instead of daily).

As a consequence of this approach, the qualifying aspects of the novel G-CSF conjugate derivatives subject of the present invention are:

employment of a protein in the conjugation reaction having a polypeptide chain corresponding to one of the G-CSF derivatives already exploited in therapy, since it is not necessary to introduce polypeptide chain mutations and/or to resort to partial or complete denaturation of the polypeptide chain;

conjugation to a biocompatible linear or branched water soluble polymer with a molecular weight ranging from 5 kDa to 60 kDa;

employment of a conjugation technique to join G-CSF to a single polymer chain on a single and specific aminoacid residue which a) is not one of the residues implied in receptor interaction, or close by to one, and b) is situated on the polypeptide chain in a position next to or close to the threonine residue at position 133 which, in the native human 174-aminoacid G-CSF, is conjugated to an oligosaccharide chain, or to the equivalent threonine-134 residue of the 175-aminoacid methionyl G-CSF derivative, or the equivalent threonine residue on G-CSF analogues.

G-CSF explicates its functions after interaction with its specific receptor (G-CSFR), which is mainly expressed on the membrane of neutrophile precursor cells, of neutrophiles and of some leukemia cell lines. Binding of G-CSF to its receptor (which stoichiometrically occurs as two G-CSF molecules for every two G-CSFR molecules) induces receptor dimerization and activates a chain of intracellular reactions which stimulates cell proliferation and nonproliferative differentiation. There are two main linkage sites on G-CSF molecules involved in receptor dimerization; the residues implied in receptorial bonds have been identified: aminoacid residues Lys 40, Phe 144, Val 48 and Leu 49 pertaining to binding site 1 and aminoacid residues Glu 19, Leu 15, Asp 112 and Leu 124 pertaining to binding site 2 (J. F. Reidhaar-Olson et al., Identification of Residues Critical to the Activity of Human Granulocyte Colony-Stimulating Factor, *Biochemistry*, 35, 9034-9041, 1996; D. C. Young et al., Characterization of the Receptor Binding Determinants of Granulocyte Colony Stimulating Factor, *Prot. Sci.*, 6, 1228-1236, 1997).

In proteins, the most exploited reactive groups for chemical conjugation to polymer chains are the ε-amino groups of lysine and the α-amino groups of the N-terminal aminoacid of the polypeptide chain. Indeed, they appear in every protein sequence with a higher or lower percentage. As far as G-CSF is concerned, there are several articles and patents describing PEG conjugation by chemical linkage to the amine groups ($NH_2$-terminal and lysinic $NH_2$). For example, WO 00/44785 describes G-CSF-PEG conjugates with PEG chains bound to lysine or to the amino N-terminal residue. This conjugation is possible in G-CSF since there are four lysines (Lys 16, Lys 23, Lys 34, Lys 40) as well as a free α-amino group at the N-terminal of the polypeptide chain and, moreover, these charged functional groups are usually accessible to the aqueous solvent.

In the case of G-CSF, the product of chemical conjugation is a mixture of several conjugates having 1-4 PEG chains linked at different positions which, to be eligible for therapy, must be separated to isolate the isomer or isomers displaying the best activity, pharmacokinetic and toxicity profiles.

As mentioned previously, there are well-known chemical conjugation techniques leading to the formation of a single conjugate through the so-called site-specific conjugation, which is only possible, though, on the α-amino group of the N-terminal aminoacid, on the free cysteine residue of the native G-CSF molecule, or on cysteine residues inserted in the polypeptide chain by site-specific mutagenesis. In the first case (as described in U.S. Pat. No. 5,985,265 and the abovementioned PEG-filgrastim compound), reaction selectivity of the N-terminal amino group is improved by carrying out the chemical reaction at a pH value of about 5: under these conditions, the ε-amino groups of lysine are only mildly nucleophilic (pKa of about 9.5), while the α-N-terminal group is still reactive and has a lower pKa value.

In the aforesaid cysteine conjugation, it is necessary to modify the G-CSF primary sequence by insertion of cysteine residues using site-specific mutagenesis reactions (as, for instance, in M. S. Rosendahl et al., 2005) or resort to denaturation of G-CSF to expose and react the native G-CSF Cys 17 (as referred to, for example, in WO 2005/099769A2).

Consequently, it can be assumed that conventional chemical conjugation procedures are not suitable for preparing site-specific mono-conjugated derivatives exhibiting the characteristics described in the present invention.

To prepare G-CSF site-specific mono-conjugate derivatives by enzymatic conjugation reactions catalyzed by transglutaminase, a preliminary analysis will verify which enzymes are of potentially use and the properties thereof, especially regarding substrate specificity.

In mammals, transglutaminases (TG-ases) are codified by a family of genes, whose products are grouped as nine structurally and functionally correlated isoenzymes (from TG-1 to TG-7; Factor XIIIA; Band 4.2) expressed in various tissues (in particular in epithelial tissues, blood and the prostate gland). They catalyze, in the presence of $Ca^{2+}$ ions, post-translational modification reactions of physiological and pathological proteins (M. Griffin et al., Transglutaminases: Nature's Biological Glues, *Biochem. J*, 368, 377-396, 2002).

Recently, microbial TG-ases isolated from different microorganisms, pertaining in particular to the genera *Streptoverticillium* spp and *Bacillus* spp, have been described where these enzymes are localized, respectively, at an extracellular level and in spores. Microbial TG-ases, as opposed to the corresponding eukaryotic enzymes, do not require $Ca^{2+}$ ion activation. Moreover, microbial TG-ases, derived from *Streptoverticillium* spp and commonly designated as MTG (Microbial transglutaminases), have also found applications in the food industry to improve the texture of meat, cheese and their derivatives (P. M. Nielsen, Reactions and Potential Industrial Applications of Transglutaminase. Review of Literature and Patent, *Food Biotechnol.*, 9, 119-156, 1995).

Both mammalian and microbial TG-ases act specifically on acyl-acceptor γ-carboxamide groups of the polypeptide chain glutamine residues. Although no specific consensus sites have been identified to date, it is commonly believed that microbial or mammalian TG-ases only recognize glutamine residues located on flexible and solvent-accessible sites of the polypeptide chain. However, there are indications that the presence of aminoacid residues having positively charged or sterically cumbersome side chains, preceding or following a glutamine residue, can positively influence recognition by the enzyme (P. Cousson et al., Factors that Govern the Specificity of Transglutaminase-Catalysed Modification of Proteins and Peptides, *Biochem. J*, 282, 929-930, 1992; T. Ohtsuka et al., Comparison of Substrate Specificities of Transglutaminase Using Synthetic Peptides as Acyl Donors, *Biosci. Biotechnol. Biochem.*, 64, 2608-2613, 2000). As regards the acyl donor moiety, both microbial and mammalian TG-ases are non-selective. In fact, not only can they react with the ε-amino groups of lysine residues on protein chains, but also with generic amines or primary aliphatic alkylamines, with a specific selectivity for primary aliphatic amines on a linear chain of at least four carbon atoms (T. Ohtsuka et al., Substrate Specificities of Microbial Transglutaminase for Primary Amines, *J. Agric. Food Chem.*, 48, 6230-6233, 2000).

*Streptoverticillium mobaraense* transglutaminase, which can be considered a prototype of microbial transglutaminases (MTG), is smaller than mammalian TG-ases. Determination of the former transglutaminase primary sequence and tertiary structure (T. Kashiwagi et al., Crystal Structure of Microbial Transglutaminase from *Streptoverticillium mobaraense*, *J. Biol. Chem.*, 277, 44252-44260, 2002) emphasized the different aminoacid structures around the active site, inferring that microbial TG-ases are not as specific as mammalian ones. On the basis of these structural studies, it has been assumed that microbial transglutaminase specificity, as regards the glutamine substrate residues, is less stringent than mammalian transglutaminase specificity, due to the higher flexibility of the protein structure forming the cleft of the active site. Moreover, being smaller probably facilitates interaction of the microbial transglutaminases with the glutamine substrate residue of the target protein.

In conclusion, according to the aforesaid conventional methods, the main requirement for glutamine residues on the protein polypeptide chain to be potential microbial or mammalian transglutaminase substrates is to be located in flexible and solvent accessible protein domains or on exposed polypeptide chains.

About one in ten of the amino acids in the G-CSF polypeptide chain is a glutamine, for a total of 17 residues. These can all be considered putative transglutaminase substrates, although the protein three-dimensional structure plays a fundamental role in rendering only a few of the glutamine residues accessible to the enzyme.

On the basis of the G-CSF three-dimensional structure, as determined by X-ray crystallography (C. P. Hill et al., The Structure of Granulocyte Colony-Stimulating Factor and its Relationship to Other Growth Factors, *Proc. Natl. Acad. Sci. USA*, 90, 5167-5171, 1993), the solvent accessibility of the side chain surface of each of the 17 G-CSF glutamine residues has been calculated employing a molecular docking technique.

As shown in Table 1 (where numeration of the Gln residues refers to the native 174-aminoacid G-CSF), six glutamine residues and, in particular, Gln residues in position 70, 173, 131, 119, 90 e 11, have at least 40% of the side chain surface accessible to solvent and can, therefore, be considered as the most probable transglutaminase substrates.

TABLE 1

| Surface accessibility to solvent of glutamine residues in G-CSF | |
|---|---|
| Gln residue position | Solvent accessible surface (%) |
| 70 | 80.7 |
| 173 | 72.0 |
| 131 | 69.6 |
| 119 | 59.5 |
| 90 | 48.6 |
| 11 | 44.1 |
| 134 | 32.5 |
| 145 | 28.7 |
| 67 | 25.5 |
| 25 | 22.5 |
| 32 | 22.3 |
| 158 | 19.5 |
| 77 | 19.3 |
| 20 | 15.6 |
| 107 | 14.3 |
| 120 | 14.6 |
| 86 | 12.8 |

The aminoacid sequence around the glutamine substrates (in particular, positively charged and polar residues) has been regarded as a contributor in determining the derivatization site (H. Sato, Enzymatic Procedure for Site-Specific PEGylation of Proteins, *Adv. Drug Deliv. Rev.*, 54, 487-504, 2002). For example, enzymatic PEGylation of IL-2 selectively takes place on position 74 (-VLNLAQ$^{74}$SK-). In G-CSF, Gln 145 residue (-SAFQ$^{145}$RRAG), with its relatively small, but still significant solvent accessible surface, can be included in those criteria and considered another potential TG-ase substrate.

In general, the relatively high number of glutamines potentially behaving as putative microbial TG-ase substrates in the G-CSF structure would complicate the TG-ase catalyzed reaction leading to a site-specific derivative mono-conjugated with a primary amino group functionalized polymer.

It has now been surprisingly discovered, and is the specific subject of the present invention, that when methionyl-G-CSF undergoes a conjugation reaction, catalyzed by a microbial transglutaminase, with 20 kDa monomethoxy-PEG-amine, a high yield of methionyl-G-CSF-PEG20 kDa site-specifically mono-conjugated on the glutamine 135 residue is obtained.

Novel, biologically-active, mono-conjugated G-CSF derivatives are hereby described and are one of the subjects of the present invention, wherein a linear or branched chain of a nonimmunogenic hydrophilic polymer functionalized with a primary amino group (for example, monomethoxy-PEG-alkyl-amine or monomethoxy-PEG-amine derivatives or analogues thereof) is site-specifically linked, by a transglutaminase enzyme catalyzed reaction, through a covalent amide bond, to the acyl moiety of the single glutamine residue adjacent to the threonine residue which, in native G-CSF, is conjugated to an oligosaccharide chain.

In particular, the mono-conjugated derivatives prepared according to the present invention are characterized by having a glutamine residue, in a position ranging from 132 to 137 and, preferably, from 132 to 134 of the native human 174-aminoacid G-CSF polypeptide chain, covalently linked to a nonimmunogenic hydrophilic polymer. More preferably, the glutamine residue in native human 174-aminoacid G-CSF is represented by the Gln$^{134}$ residue, in the 175-aminoacid methionyl-G-CSF is represented by the Gln$^{135}$ residue and, in the case of biologically active G-CSF mutants, is represented by the glutamine residue in a corresponding position on the polypeptide chain.

According to one embodiment of the present invention, the water soluble polymer is selected from linear or branched poly(ethylene glycols), poly(oxypropylenes), poly(oxyethylene)-poly(oxypropylene) block copolymers, poly(vinylpyrrolidones), poly(acryloylmorpholines), poly(saccharides) or aminocarbamyl poly(ethylene glycols).

According to another embodiment of the present invention, the hydrophilic polymer is a linear or branched monomethoxy-polyethylene glycol amine with a molecular weight ranging from 5 kDa to 40 kDa, preferably from 15 to 25 kDa, and even more preferably it is a linear monomethoxy-polyethylene glycol amine with a molecular weight of about 20 kDa. For instance, it may be a linear monomethoxy-polyethylene glycol amine of the formula:

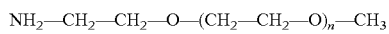

NH$_2$—CH$_2$—CH$_2$—O—(CH$_2$—CH$_2$—O)$_n$—CH$_3$ where n ranges from about 112 to 907, preferably from about 339 to 566 and, more preferably, is about 453.

According to another embodiment, the hydrophilic polymer is a aminocarbamyl polyethylene glycol with a molecular weight ranging from 5 kDa to 40 kDa, preferably between 15 and 25 kDa and, more preferably, 20 kDa. For instance, it may be an O—[methyl-poly(ethylene glycol)]-N-[2-(3-aminopropoxy)ethoxy]ethylcarbamate of the formula:

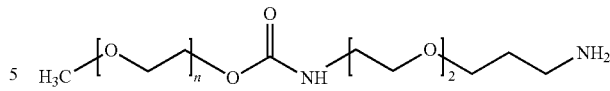

where n ranges from about 109 to 904, preferably from about 336 to 563, and, more preferably, 450.

Another subject of the present invention are G-CSF molecules possessing a stimulating activity over proliferation and differentiation of progenitor cells to mature neutrophiles derivatized by the site-specific mono-conjugated enzymatic reaction described in the previous paragraph and exploitable for the purpose of the present invention, including the native human 174-aminoacid G-CSF molecule, the 175-aminoacid met-G-CSF, with an additional methionyl residue at the N-terminal (filgrastim), or other analogous human G-CSF variants where, in comparison to the native G-CSF sequence, 1 to 15 aminoacid residues have been substituted, removed or added.

Here are two examples of G-CSF aminoacid sequences which can be used to prepare site-specific mono-conjugates according to the present invention:

```
(Met)n Thr Pro Leu Gly Pro Ala Ser Ser Leu Pro

Gln Ser Phe Leu Leu Lys Cys Leu Glu Gln

Val Arg Lys Ile Gln Gly Asp Gly Ala Ala

Leu Gln Glu Lys Leu Cys Ala Thr Tyr Lys

Leu Cys His Pro Glu Glu Leu Val Leu Leu

Gly His Ser Leu Gly Ile Pro Trp Ala Pro

Leu Ser Ser Cys Pro Ser Gln Ala Leu Gln

Leu Ala Gly Cys Leu Ser Gln Leu His Ser

Gly Leu Phe Leu Tyr Gln Gly Leu Leu Gln

Ala Leu Glu Gly Ile Ser Pro Glu Leu Gly

Pro Thr Leu Asp Thr Leu Gln Leu Asp Val

Ala Asp Phe Ala Thr Thr Ile Trp Gln Gln

Met Glu Glu Leu Gly Met Ala Pro Ala Leu

Gln Pro Thr Gln Gly Ala Met Pro Ala Phe

Ala Ser Ala Phe Gln Arg Arg Ala Gly Gly

Val Leu Val Ala Ser His Leu Gln Ser Phe

Leu Glu Val Ser Tyr Arg Val Leu Arg His

Leu Ala Gln Pro
``` where n=0 or 1 refer, respectively, to the native 174-aminoacid G-CSF and to the 175-aminoacid met-G-CSF, and the glutamine residue covalently bound to the polymer is in bold letters and underlined.

In particular, when n=0, the sequence is SEQ ID No 1, that is, the native human 174-aminoacid G-CSF sequence; when n=1, the sequence is SEQ ID No 2, that is the 175-aminoacid met-G-CSF with an additional methionyl residue at the N-terminal corresponding to filgrastim.

The enzymatic conjugation procedure, which exploits a microbial transglutaminase (for example, *Streptoverticillium* mobaraense MTG enzyme) includes the following steps, hereby mentioned as illustrative examples:

A) dissolution of G-CSF, or analogues or derivatives thereof, in a buffer solution with a pH ranging from 6 to 8;

B) addition of the hydrophilic polymer, displaying at least one primary amino function (for example, a methoxy-PEG-amine);

C) addition of MTG and reaction for 1-24 hours at a temperature ranging between 15 and 35° C., preferably 25° C.;

D) optional purification of site-specific mono-conjugated G-CSF, preferably by column chromatography.

According to one embodiment, the enzyme is used in amounts varying between 1 and 300 mU/mg G-CSF, preferably in amounts of about 250 mU/mg, and the reaction is carried out for 1-6 hours.

According to another embodiment, the enzyme is used in amounts varying between 1 and 20 mU/mg G-CSF, preferably in amounts of about 10 mU/mg, and the reaction is carried out for 12-24 hours.

Protein dissolution can be carried out in a phosphate buffer or other pH 6-8 buffer, and preferably at pH 7.4. The reaction can be carried out in the presence of additives, such as NaCl or other inorganic or organic salts (at a concentration between 1 and 200 mM) or surfactants at a concentration between 0.001 and 2%.

When the reaction was carried out using 174-aminoacid G-CSF and PEG-amine-20 kDa (as reported below in Example 1) the yield of G-CSF-PEG20 kDa mono-PEGylated derivative was greater than 80%.

Conjugated derivative characterization was carried out according to peptide mapping analysis. Sequencing of the resulting peptides confirmed that the conjugation of native G-CSF to a PEG functionalized with an amino group takes place selectively on the Gln 134 residue and yields a site-specific mono-conjugate. The G-CSF derivative, selectively mono-conjugated on glutamine 134 had a significant biological activity in vitro and demonstrated, in comparison to native G-CSF, a prolonged pharmacological activity after in vivo administration.

Moreover, met-G-CSF, selectively mono-conjugated on glutamine 135 (met-G-CSF-Gln$^{135}$-PEG20 kDa) as compared to the marketed reference product Neulasta® (produced by monoPEGylated met-G-CSF obtained by chemical PEGylation on the methionyl amino-terminal), demonstrated a higher in vitro biological activity and an equivalent pharmacokinetic profile.

Specificity and selectivity of the mono-PEGylation reaction, catalyzed by microbial transglutaminase, to the Gln 134 residue of native 174-aminoacid G-CSF or to the Gln 135 residue of the 175-aminoacid methionyl-G-CSF or to the corresponding Gln residue of G-CSF analogues, was confirmed by PEGylation studies carried out on met-G-CSF mutants, wherein one or more glutamine residues had been substituted through site-specific mutagenesis with asparagine residues. Mutants expressed in E. coli, purified to at least 95%, maintained the correct structural conformation, as demonstrated by an in vitro biological activity test in comparison to the non-mutated reference protein.

PEG conjugation, under the same reaction conditions, to met-G-CSF and two mutants thereof (Gln159Asn e Gln135Asn/Gln159Asn), whose profiles are shown in FIG. 11, has confirmed that only glutamine 135 behaves as a transglutaminase substrate, since substitution with an asparagine residue essentially inhibits the met-G-CSF PEGylation reaction.

Moreover, both G-CSF and derivatives thereof, obtained by chemical conjugation (for example, PEGylated), when stored in aqueous solution, easily originate soluble or non-soluble aggregates and, in the case of conjugated derivatives, instability increases as a function of position and conjugation techniques, of protein concentration and storage conditions (M. J. Treuheit et al., Inverse Relationship of Protein Concentration and Aggregation, Pharmac. Res., 19, 511-516, 2002; R. S. Rajan et al., Modulation of Protein Aggregation by Polyethylene Glycol Conjugation: G-CSF a Case Study, Prot. Sci., 15, 1063-1075, 2006). The new conjugated derivatives described in the present invention (for example, the derivative PEGylated on Gln 134 of native 174-aminoacid G-CSF) was stable to aggregation, both at concentrations of 5 mg/ml and at 10 mg/ml, in the presence and absence of a surfactant.

Another subject of the present invention includes pharmaceutical formulations of G-CSF derivatives and analogues thereof, mono-conjugated on a single and specific glutamine residue to nonimmunogenic hydrophilic polymers, which can include a ready-to-use sterile solution or a sterile lyophilized powder to be reconstituted for use with an appropriate solvent.

In the first case (ready-to-use sterile solution), as well as the G-CSF conjugated derivatives (for example, the mono-PEGylated derivative conjugated to Gln$^{134}$ of native G-CSF) at a concentration ranging from 1 to 10 mg/ml, preferably from 5 to 10 mg/ml, an isotonic agent selected, for example, amongst sugars such as sucrose, lactose, mannitol or sorbitol and a suitable buffering agent, to control the solution pH to 4 or 5 (preferably 5), may be also included. Another ingredient of this formulation can optionally be a non-ionic surfactant, such as Tween 20 or Tween 80.

In the case of a sterile lyophilized powder formulation to be reconstituted for use, one of its ingredients may be a bulking agent such as mannitol, trehalose, sorbitol or glycine and, if necessary, a cryoprotectant, such as trehalose or mannitol. The solvent for reconstitution can be water for injectable compounds, with or without a buffering salt to control the pH to 4 to 5.

For the purposes of the present invention:

the term "G-CSF homologue" refers to any protein with an aminoacid sequence having at least 90% homology to the aminoacid sequence of native human 174-aminoacid G-CSF. Aminoacid sequence variations of G-CSF homologues can be due to addition, subtraction, substitution or chemical modification of one or more aminoacids of the native human 174-aminoacid sequence;

the term "analogue of human G-CSF" refers to a polypeptide possessing the activity of native human G-CSF to stimulate proliferation and differentiation of progenitor cells to mature neutrophiles, whose aminoacid sequence is according to SEQ ID No 1, but where from 1 to 15 aminoacids have been removed or substituted with other aminoacids;

the term "human G-CSF derivative" refers to a polypeptide possessing the activity of native human G-CSF to stimulate proliferation and differentiation of progenitor cells to mature neutrophiles, whose aminoacid sequence is reported in SEQ ID No 1, but where one or more aminoacids of the sequence are linked to other molecules; representative examples of G-CSF derivatives are glycosilated G-CSF, filgrastim, specifically the polypeptide in SEQ ID No 2 having a methionyl residue at the N-terminal; the abovementioned terms are not mutually exclusive since G-CSF analogues, where one or more aminoacids are bound to other molecules, are also employable for the purposes of the present invention;

the term "nonimmunogenic" refers to the polymers employed for the enzymatic conjugation reaction and implies that the same polymers, when administered through the systemic route do not induce immune system activation, nor significantly cause specific anti-polymer antibodies.

The preferred embodiments of the present invention are illustrated by, but not limited to, the following examples.

EXAMPLES

Example 1

Preparation of the Site-Specific Mono-PEGylated G-CSF-Gln$^{134}$-PEG20 kDa Derivative Nonglycosilated rec-G-CSF, expressed in *E. coli*, was dissolved in 10 mM potassium dihydrogen phosphate buffer at pH 7.4 to a concentration of 1 mg/ml of protein, corresponding to about 53 µM. 20 kDa monomethoxy-poly(ethylene glycol) amine(methoxypoly(ethylene glycol) amine 20000, Fluka) was then added to the protein solution to a molar ratio of 10:1 PEG:G-CSF. After adding microbial transglutaminase (Activa WM, Ajinomoto) at a concentration of 0.024 U/ml reaction solution, the protein solution was incubated for 16 hours at room temperature under gentle agitation. After completing the reaction, the solution was diluted using 20 mM sodium acetate buffer at pH 4.0 and purified by column chromatography (CM Sepharose), eluting with a linear gradient (from 0 to 500 mM NaCl in 15 column volumes). A pool of the fractions containing monoPEGylated G-CSF was concentrated and subjected to gel filtration on a Sephadex G-25 column, eluted using 20 mM sodium acetate buffer at pH 4.0.

At the end of the process, a derivative selectively monoPEGylated on the Gln 134 residue (rec-h-G-CSF-Gln$^{134}$-PEG20 kDa) at a concentration of about 1 mg/ml, in 20 mM sodium acetate buffer at pH 4.0 was obtained.

At each preparation and purification step, a sample was analysed on a SE-HPLC column to determine the reaction yield, the degree of purification and the protein concentration. Chromatograms of the reaction mixture at the start, after 16 hours incubation at room temperature and of the purified derivative, monoPEGylated at position 134, are shown respectively in FIGS. 1, 2 and 3.

Example 2

Determination of rec-h-G-CSF-Gln$^{134}$-PEG20 kDa Conjugation Site

A purified rec-h-G-CSF-Gln$^{134}$-PEG20 kDa compound was hydrolysed enzymatically using endoproteinase GluC. It was incubated at pH 8.8 for 18 hours at a temperature of 37° C. in 120 mM NH$_4$HCO$_3$ buffer.

After digestion, the peptide mixture was analysed by polyacrylamide gel electrophoresis, which separated three electrophoretic bands (see FIG. 4): (I) migration corresponding to proteins with a molecular weight lower than 4,000 Da; (II) migration corresponding to proteins with a molecular weight of about 40,000 Da; (III) migration corresponding to proteins with a molecular weight of about 60,000 Da. The latter is the non-hydrolysed PEGylated protein residue, having a calculated molecular weight of 38,798 Da (20,000+18,798). Its migration to a higher molecular weight must be ascribed to the encumbrance of PEG20 kDa, which corresponds to a double size globular protein (40 kDa). Band II displays a strong positive reaction after treatment with barium iodide, thus indicating the presence of PEGylated peptides.

Band II was Western Blotted onto a PVDF membrane and analysed using automatic Edman degradation to determine the aminoacid sequence (see Table 2).

TABLE 2

Results of the N-terminal aminoacid sequence of the blotted SDS-PAGE Band II

| Sequence cycle | Position on the G-CSF sequence | Aminoacid |
| --- | --- | --- |
| 1 | 124 | Leucine |
| 2 | 125 | Glycine |
| 3 | 126 | Methionine |
| 4 | 127 | Alanine |
| 5 | 128 | Proline |
| 6 | 129 | Alanine |
| 7 | 130 | Leucine |
| 8 | 131 | Glutamine |
| 9 | 132 | Proline |
| 10 | 133 | Threonine |
| 11 | 134 | (*) |
| 12 | 135 | Glycine |
| 13 | 136 | Alanine |
| 14 | 137 | Methionine |
| 15 | 138 | Proline |
| 16 | 139 | Alanine |
| 17 | 140 | Phenylalanine |
| 18 | 141 | Alanine |

(*) In this cycle, no chromatographic peak corresponding to any of the standard aminoacids appeared.

From the results shown above, it can be unequivocally deduced that PEGylation specifically occurs on the Leu$^{124}$-Ala$^{141}$ peptide resulting from endoproteinase GluC hydrolysis and, more specifically, on the Gln$^{134}$ residue, corresponding to the 11$^{th}$ aminoacid of the Leu$^{124}$-Ala$^{141}$ peptide N-terminal sequence.

Example 3

Gln159Asn and Gln159Asn/Gln135Asn met-G-CSF Mutants PEGylation to PEG20 kDa-NH$_2$ by Microbial TG-ase Each nonglycosylated mutant, expressed in *E. coli*, was dissolved in 10 mM potassium dihydrogen phosphate solution at pH 7.4 and at a concentration of 1 mg protein/ml, corresponding to about 53 µM. 20 kDa monomethoxy-poly(ethylene glycol) amine(methoxypoly(ethylene glycol) amine 20000, Fluka) was then added to the protein solution to a molar ratio of 10:1 PEG:G-CSF. After adding microbial transglutaminase (Activa WM, Ajinomoto) at a concentration of 0.024 U/ml reaction solution, the protein solution was incubated for 16 hours at room temperature under gentle agitation. An aliquot of the reaction mixture was analysed on a SE-HPLC column at the beginning and the end of the reaction to determine the yield and protein concentration.

The fact that the double mutant Gln159Asn/Gln135Asn did not yield any PEGylated products, as opposed to the single mutant Gln159Asn, signifies that conjugation is specifically carried out on the glutamine at position 135 and confirms the aminoacid sequence data shown above. Chromatograms of the reaction mixture at the start and after 16 hours incubation at room temperature are respectively shown in FIGS. 5 and 6.

Example 4

Met-G-CSF PEGylation to PEG20 kDa-NH$_2$ Via Guinea Pig TG-ase

Nonglycosylated rec-G-CSF, expressed in *E. coli*, was dissolved in 100 mM tris buffer at pH 7.5 to a concentration of 1 mg protein/ml, corresponding to about 53 µM. 20 kDa monomethoxy-poly(ethylene glycol) amine (methoxypoly(ethylene glycol) amine 20000, Fluka) was then added to the protein solution to a molar ratio of 10:1 PEG:G-CSF. After the addition of Guinea Pig transglutaminase (Sigma) to a concentration of 0.3 U/ml reaction solution and 10 mM CaCl$_2$, the protein solution was incubated for 16 hours at room temperature under gentle agitation. Samples of the reaction mixture were analysed on a SE-HPLC column at the beginning and the end of the reaction to determine the yield and protein concentration.

As expected, this enzyme did not yield any PEG conjugates.

Chromatograms of the reaction mixture at the start and after 16 hours incubation at room temperature are respectively shown in FIGS. 7 and 8.

Example 5

Met-G-CSF PEGylation to PEG20 kDa-NH$_2$ Via Human Keratinocyte TG-ase

Nonglycosylated rec-G-CSF, expressed in *E. coli*, was dissolved in 100 mM tris buffer at pH 7.5 at a concentration of 0.5 mg protein/ml, corresponding to about 26.5 µM. 20 kDa monomethoxy-poly(ethylene glycol) amine(methoxypoly(ethylene glycol) amine 20000, Fluka) was then added to the protein solution to a molar ratio of 10:1 PEG:G-CSF. After the addition of human keratinocyte transglutaminase (recombinant human keratinocyte transglutaminase, N-Zyme) to a concentration of 0.5 U/ml reaction solution and 10 mM CaCl$_2$, the protein solution was incubated for 16 hours at room temperature under gentle agitation. An aliquot of the reaction mixture was analysed on a SE-HPLC column at the beginning and the end of the reaction to determine the yield and protein concentration.

As expected, this enzyme did not yield any PEG conjugates.

Example 6

Determination of In Vitro Biological Activity of Met-G-CSF-Gln$^{135}$-PEG20 kDa Met-G-CSF-Gln$^{135}$-PEG20 kDa biological activity was tested in vitro with a proliferation assay employing the murine myeloblastic cell line M-NFS60 which increases its proliferation activity in the presence of G-CSF (N. Shirafuji et al., A New Bioassay for Human Granulocyte Colony-Stimulating Factor Using Murine Myeloblastic NFS-60 Cells as Targets and Estimation of Its Level in Sera from Normal Healthy Persons and Patients with Infectious and Haematological Disorders, *Exp. Hematol.*, 17, 116-119, 1989).

M-NFS60 cells were distributed into 96-well plates at a concentration of 10$^4$ cells/well in 200 µl of culture medium (RPMI 1640, 10% FBS) containing increasing concentrations of met-G-CSF-Gln$^{135}$-PEG20 kDa (1-30 ng/ml), standard G-CSF (0.001-5 ng/ml) and N-terminally PEGylated met-G-CSF (1-30 ng/ml).

The plates were incubated at 37° C. in a 5% CO$_2$ atmosphere. After 48 hours, 20 µl of WST1 reagent were added and incubation continued for a further 4 hours under the same conditions.

The absorbance of the samples was measured in the wavelength range 420-480 nm against a (white) background using an ELISA microplate reader. The biological activity of the samples tested was calculated using standard proliferation curves and expressed as an EC$_{50}$ value (concentration that stimulates 50% of the maximum growth).

The assay results are shown in Table 3 and in FIG. 9.

TABLE 3

| | In vitro bioactivity results | | |
|---|---|---|---|
| | G-CSF Standard | MetG-CSF-NH-PEG20 KDa | MetG-CSF-Gln$^{135}$-PEG-20 kDa |
| EC50 (pg/ml) (*) | 60 | 435 | 343 |
| Residual Activity (%) | — | 13.7 | 17.4 |

(*) concentration in G-CSF equivalents.

Results demonstrated that the met-G-CSF-Gln$^{135}$-PEG20 kDa derivative, mono-conjugated to glutamine 135, had an in vitro residual activity of about 20% of the native protein, slightly higher than that of N-terminally PEGylated h-G-CSF (met-G-CSF-NH-PEG20 kDa).

Example 7

Determination of the met-G-CSF-Gln$^{135}$-PEG20 kDa Pharmacokinetic Profile

This experiment examined the long-lasting effect of met-G-CSF-Gln$^{135}$-PEG20 kDa, selectively monoPEGylated on glutamine 135, administered subcutaneously to rats, by time evaluation of the protein sera levels.

Three groups of 4 Sprague-Dawley male rats, weighing 300-350 g, were subcutaneously injected on their backs with native G-CSF, N-terminally PEGylated G-CSF (met-G-CSF-NH-PEG20 kDa) and met-G-CSF-Gln$^{135}$-PEG20 kDa.

Each of the four animals in the first group received a 0.1 mg/kg dose of G-CSF, dissolved in a pH 5 buffered saline solution containing 10 mM of acetate buffer.

Met-G-CSF-NH-PEG20 kDa (dissolved in a pH 5 buffered saline solution containing 10 mM of acetate buffer) was administered at the dose of 0.1 mg/kg, calculated as G-CSF equivalent, to each of the four animals in the second group.

Met-G-CSF-Gln$^{135}$-PEG20 kDa (dissolved in a pH 5 buffered saline solution containing 10 mM acetate buffer) was administered at the dose of 0.1 mg/kg, calculated as G-CSF equivalent, to each of the four animals in the third group.

Immediately after administration and after 1, 2, 4, 8, 24, 32, 48 and 72 hours, 0.5 ml blood samples were taken. The blood sample was processed to obtain sera which were tested with an ELISA protein immune assay (Kit ELISA: Human G-CSF Assay Kit; cod. JP27131; IBL Co. Ltd.), using h-G-CSF as a standard for the sera obtained from rats which had been administered h-G-CSF, met-G-CSF-NH-PEG20 kDa as a standard for the sera obtained from the rats in the second group and met-G-CSF-Gln$^{135}$-PEG20 kDa as a standard for the rat sera dosage for rats treated with met-G-CSF-Gln$^{135}$-PEG20 kDa.

Using the serum concentration values, pharmacokinetic profiles were calculated as reported in FIG. 10, and the AUC (area under the curve), $T_{max}$ and $C_{max}$ (peak time and concentration) and $T_{1/2}$ (half-life) were determined. The results are shown in Table 4.

TABLE 4

| Pharmacokinetic parameters | | | |
|---|---|---|---|
| | hG-CSF | Neulasta ® | MetG-CSF-Gln$^{135}$-PEG-20 kDa |
| $T_{max}$ (h) | 2 | 8 | 8 |
| $C_{max}$ (ng/ml) | 132 | 29.2 | 36.9 |
| AUC | 735 | 920 | 794 |
| $T_{1/2}$ (h) | 2.1 | 8.1 | 8.2 |

Example 8

Preparation of the Site-Specific Mono-PEGylated Met-G-CSF-Gln$^{135}$-PEG20 kDa (Filgrastim-Gln 135-PEG20 kDa) Derivative Nonglycosilated rec-met-G-CSF (filgrastim), expressed in *E. coli*, was dissolved in 10 mM potassium dihydrogen phosphate at pH 7.4 to a concentration of 1 mg protein/ml, corresponding to about 53 μM. 20 kDa monomethoxy-poly(ethylene glycol) amine(methoxypoly(ethylene glycol) amine 20000, Fluka) was then added to the protein solution to a molar ratio of 10:1 PEG:G-CSF. After adding microbial transglutaminase (Activa WM, Ajinomoto) to a concentration of 0.024 U/ml reaction solution, the protein solution was incubated for 16 hours at room temperature under gentle agitation. At the end of reaction, the solution was diluted with a 20 mM sodium acetate buffer at pH 4.0 and purified by column chromatography (CM Sepharose), eluting with a linear gradient (from 0 to 500 mM NaCl in 15 column volumes). A pool of the fractions containing monoPEGylated G-CSF was concentrated and subjected to gel filtration on a Sephadex G-25 column, eluting with a 20 mM sodium acetate buffer at pH 4.0.

At the end of the process, the derivative was selectively monoPEGylated on the Gln 135 residue (rec-h-met-G-CSF-Gln$^{135}$-PEG20 kDa) at a concentration of about 1 mg/ml in 20 mM sodium acetate buffer at pH 4.0.

Samples at each step of the preparation and purification were analysed on a SE-HPLC column to determine the reaction yield, purification factor and concentration. Chromatograms of the reaction mixture at the start, after 16 hours incubation at room temperature and of the purified derivative, monoPEGylated in position 135 (Glu135), are shown respectively in FIGS. 12, 13 and 14.

Example 9

Gln135Asn Met-G-CSF Mutant PEGylation to PEG20 kDa-NH$_2$ by Microbial TG-ase

Nonglycosylated Gln135Asn met-G-CSF mutant, expressed in *E. coli*, was dissolved in 10 mM potassium dihydrogen phosphate buffer at pH 7.4 to a concentration of 1 mg protein/ml, corresponding to about 53 μM. 20 kDa monomethoxy-poly(ethylene glycol) amine(methoxypoly (ethylene glycol) amine 20000, Fluka) was then added to the protein solution to a molar ratio of 10:1 PEG:G-CSF. After adding microbial transglutaminase (Activa WM, Ajinomoto) to a concentration of 0.024 U/ml reaction solution, the protein solution was incubated for 16 hours at room temperature under gentle agitation. Samples of the reaction mixture were analysed on a SE-HPLC column at the beginning and the end of the reaction to determine the yield and protein concentration.

Chromatograms recorded before the start of the reaction (FIG. 15) and those recorded after 16 hours (FIG. 16) were characterised by having one peak with a retention time corresponding to the unconjugated protein: hence the Gln135Asn mutant was not PEGylated.

Example 10

Gln135Asn-Thr134Gln Met-G-CSF Mutant PEGylation to PEG20 kDa-NH$_2$ by Microbial TG-ase Nonglycosylated Gln135Asn-Thr134Gln mutant, expressed in *E. coli*, was dissolved in 10 mM potassium dihydrogen phosphate buffer at pH 7.4 to a concentration of 1 mg protein/ml, corresponding to about 53 μM. 20 kDa monomethoxy-poly(ethylene glycol) amine(methoxypoly (ethylene glycol) amine 20000, Fluka) was then added to the protein solution to a molar ratio of 10:1 PEG:G-CSF. After adding microbial transglutaminase (Activa WM, Ajinomoto) to a concentration of 0.024 U/ml reaction solution, the protein solution was incubated for 16 hours at room temperature under gentle agitation. Samples of the reaction mixture were analysed on a SE-HPLC column at the beginning and the end of the reaction to determine the yield and protein concentration. The calculated PEGylation yield for the met-G-CSF-Gln134-PEG20 kDa mutant is 60%.

Chromatograms for samples taken before starting the reaction (FIG. 17) exhibited a single peak corresponding to the protein. After 16 hours incubation at 25° C. a new peak having a shorter retention time (hence higher MW) was observed, as shown by the chromatogram for a sample taken at the end of the reaction (FIG. 18).

Example 11

PEGylation of Met-G-CSF (Filgrastim) to PEG20 kDa-NH$_2$ by Using Microbial TG-ase (250 mU/ml of Protein)

This example shows that it is possible to quantitatively obtain PEGylation of filgrastim after only 2 hours reaction time, using MTG-ase in a ratio of 250 mU MTgase/mg of filgrastim.

Nonglycosilated rec-met-G-CSF (filgrastim), expressed in *E. coli*, was dissolved in 10 mM potassium dihydrogen phosphate buffer at pH 7.4 to a concentration of 1 mg protein/ml, corresponding to about 53 μM. 20 kDa monomethoxy-poly (ethylene glycol) amine(methoxypoly(ethylene glycol) amine 20000, Fluka) was then added to the protein solution to a molar ratio of 10:1 PEG:G-CSF. Microbial transglutaminase (Activa WM, Ajinomoto) was then added to the reaction mixture at a concentration of 0.25 U/ml reaction solution. The reaction was carried out under gentle agitation for 2 hours at room temperature. Samples were taken and analysed on a SE-HPLC column to determine the reaction yield. Chromatograms of the reaction mixture at the start and after 2 hours at room temperature are shown respectively in FIGS. 19 and 20.

The invention claimed is:

1. A human Granulocyte Colony Stimulating Factor (G-CSF) site-specific, mono-conjugated derivative, or an analogue thereof, wherein a glutamine residue in a position ranging from amino acid 132 to 137 of the native human 174-amino acid G-CSF polypeptide chain sequence is covalently linked to a non-immunogenic hydrophilic polymer.

2. The human G-CSF site-specific, mono-conjugated derivative according to claim 1, wherein the glutamine residue is in a position ranging from 132 to 134 of the native human 174-amino acid G-CSF polypeptide chain or in a position ranging from 133 to 135 of the 175-amino acid Met-G-CSF derivative polypeptide chain or in a corresponding position of a G-CSF homologue polypeptide chain.

3. The human G-CSF site-specific, mono-conjugated derivative according to claim 1, wherein the glutamine residue is in position 134 of the native human 174-amino acid G-CSF polypeptide chain or in position 135 of the 175-amino acid Met-G-CSF derivative polypeptide chain or in a corresponding position of a G-CSF homologue polypeptide chain.

4. The G-CSF site-specific, mono-conjugated derivative according to claim 1, wherein the conjugating non-immunogenic hydrophilic polymer is functionalized with at least one amino group.

5. The G-CSF site-specific, mono-conjugated derivative according to claim 1, wherein the non-immunogenic hydrophilic polymer is selected from linear or branched polyethylene glycols, polyoxypropylenes, polyoxyethylene-polyoxypropylene block copolymers, polyvinylpyrrolidones, polyacryloylmorpholines, polysaccharides, and aminocarbamyl polyethylene glycols.

6. The G-CSF site-specific, mono-conjugated derivative according to claim 1, wherein the non-immunogenic hydrophilic polymer is a linear or branched monomethoxy-polyethylene glycol amine having a molecular weight ranging from 5 kDa to 40 kDa.

7. The G-CSF site-specific, mono-conjugated derivative according to claim 6, wherein the non-immunogenic hydrophilic polymer is a linear or branched monomethoxy-polyethylene glycol amine having a molecular weight ranging from 15 kDa to 25 kDa.

8. The G-CSF site-specific, mono-conjugated derivative according to claim 7, wherein the non-immunogenic hydrophilic polymer is a linear monomethoxy-polyethylene glycol amine having a molecular weight of about 20 kDa.

9. The G-CSF site-specific, mono-conjugated derivative according to claim 1, wherein the non-immunogenic hydrophilic polymer is an aminocarbamyl polyethylene glycol having a molecular weight ranging from 5 kDa to 40 kDa.

10. The G-CSF site-specific, mono-conjugated derivative according to claim 9, wherein the non-immunogenic hydrophilic polymer is an amino carbamyl polyethylene glycol having a molecular weight ranging from 15 kDa to 25 kDa.

11. The human G-CSF site-specific, mono-conjugated derivative according to claim 1, having an amino acid sequence corresponding to SEQ ID NO: 1.

12. The G-CSF site-specific, mono-conjugated derivative according to claim 1, having an amino acid sequence corresponding to SEQ ID NO: 2.

13. A formulation containing comprising at least one site-specific, mono-conjugated derivative of human G-CSF, or an analogue thereof according to claim 1, together with pharmaceutically acceptable excipients and/or coadjuvants.

14. The formulation according to claim 13, which is a solution or a lyophilized powder.

15. The formulation according to claim 13, which is parenterally administrable.

16. A method for treating neutropenia, mobilizing mammalian peripheral blood haematopoietic progenitor cells, or any combination thereof, wherein the method comprises administering to a patient in need thereof an effective amount of at least one site-specific mono-conjugated derivative, or an analogue thereof according to claim 1.

17. A process for the preparation of a site-specific, mono-conjugated derivative of human G-CSF, or an analogue thereof according to claim 1, wherein the process comprises achieving an amide bond reaction between the glutamine residue and the non-immunogenic hydrophilic polymer in the presence of a transglutaminase activity enzyme.

18. The process according to claim 17, wherein said transglutaminase activity enzyme is of bacterial origin.

19. The process according to claim 18, wherein said transglutaminase activity enzyme is *Streptoverticillium mobaraense* transglutaminase.

20. The process according to claim 17, wherein said amide bond reaction is carried out in a buffered saline solution at a pH ranging between 6 and 8.

21. The process according to claim 20, wherein said amide bond reaction is carried out in a buffered saline solution at a pH of about 7.4.

22. The process according to claim 17 wherein said amide bond reaction is carried out for 1-24 hours.

23. The process according to claim 17, wherein said transglutaminase activity enzyme is used in amounts varying between 1 and 300 mU/mg G-CSF derivative, or an analogue thereof, and wherein said reaction is carried out for 1-6 hours.

24. The process according to claim 23, wherein said transglutaminase activity enzyme is used in amounts of about 250 mU/mg.

25. The process according to claim 17, wherein said transglutaminase activity enzyme is used in amounts varying between 1 and 20 mU/mg G-CSF derivative, or an analogue thereof, and wherein said reaction is carried out for 12-24 hours.

26. The process according to claim 25, wherein said transglutaminase activity enzyme is used in amounts of about 10 mU/mg.

27. The process according to claim 17, wherein said amide bond reaction is carried out at a temperature ranging from 15 to 35° C.

28. The process according to claim 27, wherein said amide bond reaction is carried out at a temperature of about 25° C.

29. The process according to claim 17, wherein said amide bond reaction is carried out in the presence of inorganic or organic salts, or surfactants, or any combination thereof.

30. The process according to claim 29, wherein said inorganic and/or organic salts are present in a concentration varying between 0 and 200 mM and said surfactants are present in a concentration varying between 0 and 2%.

31. The process according to claim 29, wherein said inorganic salt is NaCl.

32. The process according to claim 17, wherein said transglutaminase activity enzyme or site-specific mono-conjugated derivative of human G-CSF, or an analogue thereof, is of recombinant origin.

* * * * *

SEQUENCE LISTING

<160> NUMBER OF SEQ ID NOS: 2

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 175
<212> TYPE: PRT
<213> ORGANISM: Artificial Sequence
<220> FEATURE:
<223> OTHER INFORMATION: Human G-CSF with an additional methionyl
      residue at the N-terminus

<400> SEQUENCE: 2

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

```
Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```